United States Patent
Strack-Logue et al.

(10) Patent No.: US 10,144,942 B2
(45) Date of Patent: Dec. 4, 2018

(54) MODIFICATION OF RNA-RELATED ENZYMES FOR ENHANCED PRODUCTION

(71) Applicant: Translate Bio, Inc., Lexington, MA (US)

(72) Inventors: Bettina Strack-Logue, Lexington, MA (US); Frank DeRosa, Lexington, MA (US); Michael Heartlein, Lexington, MA (US)

(73) Assignee: Translate Bio, Inc., Lexington, MA (US)

( * ) Notice: Subject to any disclaimer, the term of this patent is extended or adjusted under 35 U.S.C. 154(b) by 0 days.

(21) Appl. No.: 15/294,249

(22) Filed: Oct. 14, 2016

(65) Prior Publication Data

US 2017/0159093 A1   Jun. 8, 2017

Related U.S. Application Data

(60) Provisional application No. 62/241,350, filed on Oct. 14, 2015.

(51) Int. Cl.
*C12P 19/34* (2006.01)
*C12N 9/12* (2006.01)
*C07K 14/47* (2006.01)
*C12N 15/62* (2006.01)

(52) U.S. Cl.
CPC .............. *C12P 19/34* (2013.01); *C07K 14/47* (2013.01); *C12N 9/1241* (2013.01); *C12N 15/62* (2013.01); *C12Y 207/0705* (2013.01); *C07K 2319/35* (2013.01); *C07K 2319/95* (2013.01)

(58) Field of Classification Search
None
See application file for complete search history.

(56) References Cited

U.S. PATENT DOCUMENTS

| | | | |
|---|---|---|---|
| 5,705,385 A | 1/1998 | Bally et al. | |
| 5,976,567 A | 11/1999 | Wheeler | |
| 5,981,501 A | 11/1999 | Wheeler et al. | |
| 6,534,484 B1 | 3/2003 | Wheeler et al. | |
| 6,815,432 B2 | 11/2004 | Wheeler et al. | |
| 7,422,902 B1 | 9/2008 | Wheeler et al. | |
| 7,655,413 B2 * | 2/2010 | Butt | C07K 14/00 435/7.1 |
| 7,745,651 B2 | 6/2010 | Heyes et al. | |
| 7,799,565 B2 | 9/2010 | MacLachlan et al. | |
| 7,803,397 B2 | 9/2010 | Heyes et al. | |
| 7,901,708 B2 | 3/2011 | MacLachlan et al. | |
| 8,101,741 B2 | 1/2012 | MacLachlan et al. | |
| 8,188,263 B2 | 5/2012 | MacLachlan et al. | |
| 8,236,943 B2 | 8/2012 | Lee et al. | |
| 8,329,070 B2 | 12/2012 | MacLachlan et al. | |
| 8,513,403 B2 | 8/2013 | MacLachlan et al. | |
| 8,569,256 B2 | 10/2013 | Heyes et al. | |
| 8,710,200 B2 | 4/2014 | Schrum et al. | |
| 8,822,663 B2 | 9/2014 | Schrum et al. | |
| 8,853,377 B2 | 11/2014 | Guild et al. | |
| 8,883,202 B2 | 11/2014 | Manoharan et al. | |
| 8,936,942 B2 | 1/2015 | Heyes et al. | |
| 8,980,864 B2 | 3/2015 | Hoge et al. | |
| 8,999,351 B2 | 4/2015 | Manoharan et al. | |
| 8,999,950 B2 | 4/2015 | MacLachlan et al. | |
| 9,018,187 B2 | 4/2015 | Heyes et al. | |
| 9,051,567 B2 | 6/2015 | Fitzgerald et al. | |
| 9,061,059 B2 | 6/2015 | Chakraborty et al. | |
| 9,074,208 B2 | 7/2015 | MacLachlan et al. | |
| 9,089,604 B2 | 7/2015 | Chakraborty et al. | |
| 9,095,552 B2 | 8/2015 | Chakraborty et al. | |
| 9,107,886 B2 | 8/2015 | Chakraborty et al. | |
| 9,114,113 B2 | 8/2015 | Chakraborty et al. | |
| 9,181,319 B2 | 11/2015 | Schrum et al. | |
| 9,186,325 B2 | 11/2015 | Manoharan et al. | |
| 9,186,372 B2 | 11/2015 | de Fougerolles et al. | |
| 9,187,748 B2 | 11/2015 | Geisbert et al. | |
| 9,192,651 B2 | 11/2015 | Chakraborty et al. | |
| 9,220,755 B2 | 12/2015 | Chakraborty et al. | |
| 9,220,792 B2 | 12/2015 | Chakraborty et al. | |
| 9,233,141 B2 | 1/2016 | Chakraborty et al. | |
| 9,254,311 B2 | 2/2016 | Bancel et al. | |
| 9,295,689 B2 | 3/2016 | de Fougerolles et al. | |
| 9,301,993 B2 | 4/2016 | Chakraborty et al. | |
| 9,303,079 B2 | 4/2016 | Chakraborty et al. | |
| 9,334,328 B2 | 5/2016 | Schrum et al. | |
| 9,345,780 B2 | 5/2016 | Manoharan et al. | |
| 9,352,042 B2 | 5/2016 | Heyes et al. | |
| 9,352,048 B2 | 5/2016 | Manoharan et al. | |
| 9,364,435 B2 | 6/2016 | Yaworski et al. | |
| 9,394,234 B2 | 7/2016 | Chen et al. | |
| 9,404,127 B2 | 8/2016 | Yaworski et al. | |
| 9,428,751 B2 | 8/2016 | MacDonald et al. | |
| 9,464,124 B2 | 10/2016 | Bancel et al. | |
| 2002/0192651 A1 | 12/2002 | Wheeler et al. | |
| 2003/0181410 A1 | 9/2003 | Wheeler et al. | |
| 2004/0142025 A1 | 7/2004 | MacLachlan et al. | |
| 2006/0008910 A1 | 1/2006 | MacLachlan et al. | |
| 2006/0083780 A1 | 4/2006 | Heyes et al. | |
| 2007/0135372 A1 | 6/2007 | MacLachlan et al. | |
| 2009/0270481 A1 | 10/2009 | MacLachlan et al. | |

(Continued)

FOREIGN PATENT DOCUMENTS

| | | |
|---|---|---|
| CA | 2807 552 | 9/2012 |
| EP | 1519 714 | 10/2010 |

(Continued)

OTHER PUBLICATIONS

Ho et al. (Journal of Virology vol. 74, No. 12, pp. 5486-5494, 2000).*

(Continued)

*Primary Examiner* — Richard G Hutson
(74) *Attorney, Agent, or Firm* — Proskauer Rose LLP; Fangli Chen; Kimberly A. Reynolds

(57) ABSTRACT

The present invention provides, among other things, methods and compositions for large-scale production of capped mRNA using SUMO-Guanylyl Transferase fusion protein.

1 Claim, 2 Drawing Sheets

Specification includes a Sequence Listing.

(56) References Cited

U.S. PATENT DOCUMENTS

| | | |
|---|---|---|
| 2010/0041152 A1 | 2/2010 | Wheeler et al. |
| 2011/0256175 A1 | 10/2011 | Hope et al. |
| 2011/0311583 A1 | 12/2011 | Manoharan et al. |
| 2012/0065252 A1 | 3/2012 | Schrum et al. |
| 2012/0128760 A1 | 5/2012 | Manoharan et al. |
| 2012/0142756 A1 | 6/2012 | Guild et al. |
| 2012/0202871 A1 | 8/2012 | Heyes et al. |
| 2012/0237975 A1 | 9/2012 | Schrum et al. |
| 2012/0251618 A1 | 10/2012 | Schrum et al. |
| 2012/0328668 A1 | 12/2012 | MacLachlan et al. |
| 2013/0195967 A1 | 8/2013 | Guild et al. |
| 2013/0237594 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2014/0010861 A1 | 1/2014 | Bancel et al. |
| 2014/0044772 A1 | 2/2014 | MacLachlan et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0171485 A1 | 6/2014 | Bancel et al. |
| 2014/0179756 A1 | 6/2014 | MacLachlan et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221465 A1 | 8/2014 | Bancel et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0294937 A1 | 10/2014 | MacLachlan et al. |
| 2014/0343129 A1 | 11/2014 | de Fougerolles et al. |
| 2015/0005372 A1 | 1/2015 | Hoge et al. |
| 2015/0017211 A1 | 1/2015 | de Fougerolles et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0111945 A1 | 4/2015 | Geisbert et al. |
| 2015/0166465 A1 | 6/2015 | Chen et al. |
| 2015/0190515 A1 | 7/2015 | Manoharan et al. |
| 2015/0265708 A1 | 9/2015 | Manoharan et al. |
| 2015/0315541 A1 | 11/2015 | Bancel et al. |
| 2015/0315584 A1 | 11/2015 | Macdonald et al. |
| 2015/0366997 A1 | 12/2015 | Guild et al. |
| 2016/0095924 A1 | 4/2016 | Hope et al. |
| 2016/0114011 A1 | 4/2016 | Bancel et al. |
| 2016/0115477 A1 | 4/2016 | MacLachlan et al. |
| 2016/0115483 A1 | 4/2016 | MacLachlan et al. |
| 2016/0136236 A1 | 5/2016 | Hoge et al. |
| 2016/0151284 A1 | 6/2016 | Heyes et al. |
| 2016/0158385 A1 | 6/2016 | Bancel et al. |
| 2016/0193299 A1 | 7/2016 | de Fougerolles et al. |
| 2016/0194368 A1 | 7/2016 | Hoge et al. |
| 2016/0194625 A1 | 7/2016 | Hoge et al. |
| 2016/0199485 A1 | 7/2016 | Manoharan et al. |
| 2016/0213785 A1 | 7/2016 | Manoharan et al. |
| 2016/0237108 A1 | 8/2016 | Fraley et al. |
| 2016/0237134 A1 | 8/2016 | Hoge et al. |
| 2016/0250354 A1 | 9/2016 | Manoharan et al. |
| 2016/0251681 A1 | 9/2016 | Yaworski et al. |
| 2016/0256567 A1 | 9/2016 | Heyes et al. |
| 2016/0256568 A1 | 9/2016 | Heyes et al. |
| 2016/0264971 A1 | 9/2016 | Geisbert et al. |
| 2016/0274089 A1 | 9/2016 | Ciufolini et al. |
| 2016/0304552 A1 | 10/2016 | Roy et al. |
| 2016/0317647 A1 | 11/2016 | Ciaramella et al. |
| 2016/0317676 A1 | 11/2016 | Hope et al. |

FOREIGN PATENT DOCUMENTS

| | | |
|---|---|---|
| EP | 2449 106 | 5/2012 |
| EP | 2338 478 | 6/2013 |
| EP | 2823 809 | 1/2015 |
| WO | WO2002/090495 | 11/2002 |
| WO | WO2005/026372 | 3/2005 |
| WO | WO2005/121348 | 12/2005 |
| WO | WO2009/127060 | 10/2006 |
| WO | WO2010/042877 | 4/2010 |
| WO | WO2011/141705 | 11/2011 |
| WO | WO2012/019168 | 2/2012 |
| WO | WO2012/135805 | 10/2012 |
| WO | WO2012/170930 | 12/2012 |
| WO | WO2013/039857 | 3/2013 |
| WO | WO2013/039861 | 3/2013 |
| WO | WO2013/090186 | 6/2013 |
| WO | WO2013/101690 | 7/2013 |
| WO | WO2013/126803 | 8/2013 |
| WO | WO2013/130161 | 9/2013 |
| WO | WO2013/151663 | 10/2013 |
| WO | WO2013/151664 | 10/2013 |
| WO | WO2013/151666 | 10/2013 |
| WO | WO2013/151667 | 10/2013 |
| WO | WO2013/151668 | 10/2013 |
| WO | WO2013/151670 | 10/2013 |
| WO | WO2013/151671 | 10/2013 |
| WO | WO2013/151672 | 10/2013 |
| WO | WO2013/151736 | 10/2013 |
| WO | WO2014/028429 | 2/2014 |
| WO | WO2014/089486 | 6/2014 |
| WO | WO2014/113089 | 7/2014 |
| WO | WO2014/144039 | 9/2014 |
| WO | WO2014/144711 | 9/2014 |
| WO | WO2014/144767 | 9/2014 |
| WO | WO2014/152027 | 9/2014 |
| WO | WO2014/152030 | 9/2014 |
| WO | WO2014/152031 | 9/2014 |
| WO | WO2014/152211 | 9/2014 |
| WO | WO2014/152540 | 9/2014 |
| WO | WO2014/158795 | 10/2014 |
| WO | WO2014/159813 | 10/2014 |
| WO | WO2015/006747 | 1/2015 |
| WO | WO2015/048744 | 4/2015 |
| WO | WO2015/051169 | 4/2015 |
| WO | WO2015/051173 | 4/2015 |
| WO | WO2015/058069 | 4/2015 |
| WO | WO2015/085318 | 6/2015 |
| WO | WO2015/089511 | 6/2015 |
| WO | WO2015/011633 | 1/2016 |
| WO | WO2016/054421 | 4/2016 |
| WO | WO2016/071857 | 5/2016 |
| WO | WO2016/077123 | 5/2016 |
| WO | WO2016/077125 | 5/2016 |
| WO | WO2016/118724 | 7/2016 |
| WO | WO2016/118725 | 7/2016 |

(56) References Cited

FOREIGN PATENT DOCUMENTS

| WO | WO2016/154127 | 9/2016 |
|----|---------------|--------|
| WO | WO2016/164762 | 10/2016 |

OTHER PUBLICATIONS

Tsukamoto et al. (Biochemical and Biophysical Research Communications, vol. 243, pp. 101-108, 1998).*
Anonymous, SUMOpro-3 Gene Fusion Technology—Product Manual, Jan. 28, 2014 (Jan. 28, 2014), pp. 1-10.
Fresco, L. D., et al., Active Site of the mRNA-Capping Enzyme Guanylyltransferase From *Saccharomyces cerevisiae*: Similarity to the Nucleotidyl Attachment Motif of DNA and RNA Ligases, Proceedings of the National Academy of Science, National Academy of Sciences, US, vol. 91, Jul. 1, 1994 (Jul. 1, 1994), pp. 6624-6628.
Guo P., et al., Interaction and Mutual Stabilization of the Two Subunits of Vaccinia Virus mNRA Capping Enzyme Coexpressed in *Escherichia coli*, Proceedings of the National Academy of Sciences, National Academy of Sciences, US, vol. 87, No. 11, Jun. 1, 1990 (Jun. 1, 1990), pp. 4023-4027.
Kyrieleis Otto, J.P., et al., Crystal Structure of Vaccinia Virus mRNA Capping Enzyme Provides Insights into the Mechanism and Evolution of the Capping Apparatus, vol. 22, No. 3, Mar. 4, 2014 (Mar. 4, 2014), pp. 452-456.

* cited by examiner

Cap 0

← mRNA

Cap 1

← mRNA

```
                         SEQUENCE LISTING

<160> NUMBER OF SEQ ID NOS: 8

<210> SEQ ID NO 1
<211> LENGTH: 90
<212> TYPE: PRT
<213> ORGANISM: Artificial Sequence
<220> FEATURE:
<223> OTHER INFORMATION: chemically synthesized polypeptide

<400> SEQUENCE: 1

Glu Glu Lys Pro Lys Glu Gly Val Lys Thr Glu Asn Asp His Ile Asn
1               5                   10                  15

Leu Lys Val Ala Gly Gln Asp Gly Ser Val Val Gln Phe Lys Ile Lys
            20                  25                  30

Arg His Thr Pro Leu Ser Lys Leu Met Lys Ala Tyr Cys Glu Arg Gln
        35                  40                  45

Gly Leu Ser Met Arg Gln Ile Arg Phe Arg Phe Asp Gly Gln Pro Ile
    50                  55                  60

Asn Glu Thr Asp Thr Pro Ala Gln Leu Glu Met Glu Asp Glu Asp Thr
65                  70                  75                  80

Ile Asp Val Phe Gln Gln Gln Thr Gly Gly
                85                  90

<210> SEQ ID NO 2
<211> LENGTH: 2588
<212> TYPE: DNA
<213> ORGANISM: Artificial Sequence
<220> FEATURE:
<223> OTHER INFORMATION: chemically synthesized oligonucleotide

<400> SEQUENCE: 2
agatggaaga tgaagatacc atcgacgtct ttcagcaaca gaccggtggt atggatgcta      60
acgtcgttag cagcagcacc attgcgactt acattgatgc actggccaaa aacgcatctg     120
agcttgagca gcgcagcacc gcctacgaga tcaataacga attggagctg gttttcatta     180
aaccgccgct gatcacgctg acgaacgtcg tgaacattag cacgattcaa gagagcttta     240
ttcgtttcac cgttaccaat aaagaaggcg tgaagatccg taccaagatt ccgctgagca     300
aagtgcatgg tctggacgtg aaaaatgtgc agctggttga tgcgatcgat aacatcgtgt     360
```

```
gggagaagaa atctttggtc acggaaaatc gtctgcacaa ggaatgtctg ctgcgtctgt     420
caaccgaaga acgccacatc ttcctggact acaagaagta tggttccagc atccgtctgg     480
aactggtgaa cctgattcag gcaaagacca agaacttcac cattgacttc aaactgaagt     540
atttcctggg ctctggtgca cagagcaaat ccagcttgtt gcacgcgatt aaccatccga     600
agagccgtcc gaatacgagc ctggagatcg aattcacgcc gcgtgataac gaaaccgttc     660
cgtacgatga gctgattaaa gaactgacga cgttgagccg ccacatcttt atggccagcc     720
cggaaaacgt gatccttagc ccgcctatca atgcgccgat taaaacccttt atgttaccga     780 aacaagacat tgtgggtctg gacctggaaa acctgtacgc ggtcaccaaa acggacggca     840
ttccgatcac gattcgtgtt accagcaatg gtctgtactg ctatttcact catttgggct     900
atatcattcg ttatccggtg aaacgcatca ttgattctga ggttgtcgtt ttcggcgaag     960
cagtcaagga caagaattgg actgtgtacc tgatcaaatt gattgaaccg gttaacgcca    1020
tcaatgaccg cctggaagag tcgaaatatg ttgaaagcaa actggtggat atttgtgatc    1080
gtatcgtgtt caagagcaag aaatatgaag gcccgttcac cacgaccagc gaagttgttg    1140
acatgctgag cacctatctg ccgaaacaac ctgagggtgt gattctgttt tactccaagg    1200
gtccgaagag caacattgat ttcaaaatca gaaagagaa taccattgat cagaccgcca    1260
acgttgtgtt ccgctatatg tccagcgagc ctatcatttt cggtgagtcg agcatctttg    1320
ttgaatacaa aaagtttagc aacgataagg gttttccgaa agaatacggt tccggtaaga    1380
ttgtgttgta caacggcgtc aattatctga caacatcta ctgtctggag tacatcaata    1440
cccataacga agttggcatt aagtctgttg tcgtcccgat caaattcatc gcggagttcc    1500
tggttaacgg tgagattctg aagccgcgta ttgataaaac tatgaaatac attaactccg    1560
aagattacta cggtaatcag cataacatca tcgtcgagca cttgcgtgat caaagcatta    1620
agatcggtga catctttaac gaagataagc tgagcgatgt aggccaccag tatgcgaaca    1680
atgacaaatt tcgcctgaat ccggaagtca gctactttac gaataagcgc acccgtggtc    1740
cactgggtat cctgagcaat tatgttaaaa ccctgttgat ttccatgtac tgctccaaaa    1800
cgttcctgga cgacagcaac aagcgcaaag ttctggcgat cgacttcggt aatggtgccg    1860
atctggagaa gtactttat ggtgagatcg cattgctggt tgctaccgac ccggatgcag    1920
atgcgatcgc ccgtggcaac gagcgttaca ataagctgaa tagcggtatc aagaccaaat    1980
actacaaatt cgactatatt caagagacga tccgctcgga cacctttgta tccagcgtgc    2040
gtgaggtgtt ttacttcggt aaattcaaca tcattgactg gcaattcgcc attcactata    2100
gctttcaccc acgccactat gcgacggtca tgaacaacct gtctgagctg accgcgagcg    2160
gcggtaaagt tctgatcacc acgatggacg gtgacaagct gtctaaactg accgacaaaa    2220
agaccttcat tattcacaaa aatctcccgt cgagcgagaa ttacatgtcc gtcgaaagaa    2280
ttgcggacga ccgtattgtt gtctacaacc gagcactat gtcgaccca atgaccgagt    2340 atatcatcaa aaagaatgac attgtgcgtg tctttaatga atacggtttt gtgctggtcg    2400
acaacgtcga ttttgcgacc atcatcgaga gaagcaagaa attcattaat ggcgcttcta    2460
cgatggaaga tcgcccgagc acgcgtaact tctttgagct gaatcgtggc gcgattaagt    2520
gcgagggcct ggacgtcgag gatctgctgt cgtattacgt ggtttatgtg tttagcaaac    2580
gttaatga                                                            2588
```

<210> SEQ ID NO 3

<211> LENGTH: 867
<212> TYPE: DNA
<213> ORGANISM: Artificial Sequence
<220> FEATURE:
<223> OTHER INFORMATION: chemically synthesized oligonucleotide

<400> SEQUENCE: 3

```
atggacgaaa ttgtcaagaa tatccgtgaa ggtacccacg ttttactgcc attctacgag      60
acgctgccgg aactgaacct gagcctgggt aaaagccctc tgccgagcct ggagtatggt     120
gcgaactatt ttctgcagat ttcccgtgta acgatttga accgcatgcc gacggacatg     180
ctgaaactgt tcacccacga catcatgctg ccggaatctg atctggataa agtttacgag     240
atcttgaaaa tcaattcagt gaagtactat ggccgtagca ccaaggccga tgcggtggtc     300
gcagacctga gcgcgcgtaa caaactgttt aaacgtgaac gtgacgcaat taagagcaat     360
aaccatctga ccgagaacaa tttgtacatc agcgactaca agatgttgac ttttgacgtg     420
tttcgtccgc tgttcgactt tgttaatgag aaatactgca ttatcaagct gccgacgttg     480
tttggtcgcg gcgtcattga tacgatgcgc atttactgct ctctcttcaa gaatgtgcgc     540
ctgctgaagt gtgtctccga cagctggctg aaagatagcg ctattatggt tgcgagcgac     600
gtgtgtaaaa agaacctgga tctgttcatg agccacgtga gagcgttac caaaagcagc     660
agctggaaag acgttaacag cgtccagttc tccattctga ataacccggt cgataccgag     720
tttatcaaca agttccttga attcagcaat cgcgtttatg aggccctgta ttacgttcat     780
agcctgctgt atagctccat gacctctgat agcaaatcga tcgagaataa acaccaacgt     840
cgtctggtga aactgctgct gtaatga                                         867
```

<210> SEQ ID NO 4
<211> LENGTH: 2844
<212> TYPE: DNA
<213> ORGANISM: Artificial Sequence
<220> FEATURE:
<223> OTHER INFORMATION: chemically synthesized oligonucleotide

<400> SEQUENCE: 4

```
atgggccatc atcatcacca tcacggcagc ctgcaagaag agaaaccgaa agagggcgtt      60
aagaccgaga atgaccacat taacctgaag gtcgctggtc aagatggcag cgtggtgcag     120
tttaagatca agcgtcacac gccgttgagc aagctgatga aggcttactg cgagcgtcag     180
ggtctgagca tgcgtcagat ccgctttcgt ttcgatggcc agccgatcaa tgagactgac     240
accccagcgc aactggagat ggaagatgaa gataccatcg acgtctttca gcaacagacc     300
ggtggtatgg atgctaacgt cgttagcagc agcaccattg cgacttacat tgatgcactg     360
gccaaaaacg catctgagct tgagcagcgc agcaccgcct acgagatcaa taacgaattg     420
gagctggttt tcattaaacc gccgctgatc acgctgacga acgtcgtgaa cattagcacg     480
attcaagaga gctttattcg tttcaccgtt accaataaag aaggcgtgaa gatccgtacc     540
aagattccgc tgagcaaagt gcatggtctg acgtgaaaa atgtgcagct ggttgatgcg     600
atcgataaca tcgtgtggga agaaaatctt ttggtcacgg aaaatcgtct gcacaaggaa     660
tgtctgctgc gtctgtcaac cgaagaacgc acatcttcc tggactacaa gaagtatggt     720
tccagcatcc gtctggaact ggtgaacctg attcaggcaa gaccaagaa cttcaccatt     780
gacttcaaac tgaagtattt cctgggctct ggtgcacaga gcaaatccag cttgttgcac     840
gcgattaacc atccgaagag ccgtccgaat acgagcctgg agatcgaatt cacgccgcgt     900
gataacgaaa ccgttccgta cgatgagctg attaaagaac tgacgacgtt gagccgccac     960
```

```
atctttatgg ccagcccgga aaacgtgatc cttagcccgc ctatcaatgc gccgattaaa    1020
acctttatgt taccgaaaca agacattgtg ggtctggacc tggaaaacct gtacgcggtc    1080
accaaaacgg acggcattcc gatcacgatt cgtgttacca gcaatggtct gtactgctat    1140
ttcactcatt tgggctatat cattcgttat ccggtgaaac gcatcattga ttctgaggtt    1200
gtcgttttcg gcgaagcagt caaggacaag aattggactg tgtacctgat caaattgatt    1260
gaaccggtta acgccatcaa tgaccgcctg aagagtcga aatatgttga aagcaaactg    1320
gtggatattt gtgatcgtat cgtgttcaag agcaagaaat atgaaggccc gttcaccacg    1380
accagcgaag ttgttgacat gctgagcacc tatctgccga acaacctga gggtgtgatt    1440 ctgttttact ccaagggtcc gaagagcaac attgatttca aaatcaagaa agagaatacc    1500
attgatcaga ccgccaacgt tgtgttccgc tatatgtcca gcgagcctat cattttcggt    1560
gagtcgagca tctttgttga atacaaaaag tttagcaacg ataagggttt tccgaaagaa    1620
tacggttccg gtaagattgt gttgtacaac ggcgtcaatt atctgaacaa catctactgt    1680
ctggagtaca tcaatacccca taacgaagtt ggcattaagt ctgttgtcgt cccgatcaaa    1740
ttcatcgcgg agttcctggt taacggtgag attctgaagc cgcgtattga taaaactatg    1800
aaatacatta actccgaaga ttactacggt aatcagcata acatcatcgt cgagcacttg    1860
cgtgatcaaa gcattaagat cggtgacatc tttaacgaag ataagctgag cgatgtaggc    1920
caccagtatg cgaacaatga caaatttcgc ctgaatccgg aagtcagcta ctttacgaat    1980
aagcgcaccc gtggtccact gggtatcctg agcaattatg ttaaaacccct gttgatttcc    2040 atgtactgct ccaaaacgtt cctggacgac agcaacaagc gcaaagttct ggcgatcgac    2100
ttcggtaatg gtgccgatct ggagaagtac tttatggtg agatcgcatt gctggttgct    2160
accgacccgg atgcagatgc gatcgcccgt ggcaacgagc gttacaataa gctgaatagc    2220
ggtatcaaga ccaaatacta caaattcgac tatattcaag agacgatccg ctcggacacc    2280
tttgtatcca gcgtgcgtga ggtgtttttac ttcggtaaat tcaacatcat tgactggcaa    2340
ttcgccattc actatagctt tcacccacgc cactatgcga cggtcatgaa caacctgtct    2400
gagctgaccg cgagcggcgg taaagttctg atcaccacga tggacggtga caagctgtct    2460
aaactgaccg acaaaaagac cttcattatt cacaaaaatc tcccgtcgag cgagaattac    2520
atgtccgtcg aaaagattgc ggacgaccgt attgttgtct acaacccgag cactatgtcg    2580
accccaatga ccgagtatat catcaaaaag aatgacattg tgcgtgtctt taatgaatac    2640
ggttttgtgc tggtcgacaa cgtcgatttt gcgaccatca tcgagagaag caagaaattc    2700
attaatggcg cttctacgat ggaagatcgc ccgagcacgc gtaacttctt tgagctgaat    2760
cgtggcgcga ttaagtgcga gggcctggac gtcgaggatc tgctgtcgta ttacgtggtt    2820
tatgtgttta gcaaacgtta atga                                           2844
```

<210> SEQ ID NO 5
<211> LENGTH: 220
<212> TYPE: DNA
<213> ORGANISM: Artificial Sequence
<220> FEATURE:
<223> OTHER INFORMATION: chemically synthesized oligonucleotide

<400> SEQUENCE: 5

```
gaagagaaac cgaaagaggg cgttaagacc gagaatgacc acattaacct gaaggtcgct      60
ggtcaagatg gcagcgtggt gcagtttaag atcaagcgtc acacgccgtt gagcaagctg     120
```

```
atgaaggctt actgcgagcg tcagggtctg agcatgcgtc agatccgctt tcgtttcgat    180
ggccagccga tcaatgagac tgacacccca gcgcaactgg                          220
```

<210> SEQ ID NO 6
<211> LENGTH: 844
<212> TYPE: PRT
<213> ORGANISM: Artificial Sequence
<220> FEATURE:
<223> OTHER INFORMATION: chemically synthesized polypeptide

<400> SEQUENCE: 6

```
Met Asp Ala Asn Val Val Ser Ser Thr Ile Ala Thr Tyr Ile Asp
1               5                   10                  15

Ala Leu Ala Lys Asn Ala Ser Glu Leu Glu Gln Arg Ser Thr Ala Tyr
                20                  25                  30

Glu Ile Asn Asn Glu Leu Glu Leu Val Phe Ile Lys Pro Pro Leu Ile
            35                  40                  45

Thr Leu Thr Asn Val Val Asn Ile Ser Thr Ile Gln Glu Ser Phe Ile
        50                  55                  60

Arg Phe Thr Val Thr Asn Lys Glu Gly Val Lys Ile Arg Thr Lys Ile
65                  70                  75                  80

Pro Leu Ser Lys Val His Gly Leu Asp Val Lys Asn Val Gln Leu Val
                85                  90                  95

Asp Ala Ile Asp Asn Ile Val Trp Glu Lys Lys Ser Leu Val Thr Glu
            100                 105                 110

Asn Arg Leu His Lys Glu Cys Leu Leu Arg Leu Ser Thr Glu Glu Arg
        115                 120                 125

His Ile Phe Leu Asp Tyr Lys Lys Tyr Gly Ser Ser Ile Arg Leu Glu
    130                 135                 140

Leu Val Asn Leu Ile Gln Ala Lys Thr Lys Asn Phe Thr Ile Asp Phe
145                 150                 155                 160

Lys Leu Lys Tyr Phe Leu Gly Ser Gly Ala Gln Ser Lys Ser Ser Leu
                165                 170                 175

Leu His Ala Ile Asn His Pro Lys Ser Arg Pro Asn Thr Ser Leu Glu
            180                 185                 190

Ile Glu Phe Thr Pro Arg Asp Asn Glu Thr Val Pro Tyr Asp Glu Leu
        195                 200                 205

Ile Lys Glu Leu Thr Thr Leu Ser Arg His Ile Phe Met Ala Ser Pro
    210                 215                 220

Glu Asn Val Ile Leu Ser Pro Pro Ile Asn Ala Pro Ile Lys Thr Phe
225                 230                 235                 240

Met Leu Pro Lys Gln Asp Ile Val Gly Leu Asp Leu Glu Asn Leu Tyr
                245                 250                 255

Ala Val Thr Lys Thr Asp Gly Ile Pro Ile Thr Ile Arg Val Thr Ser
            260                 265                 270

Asn Gly Leu Tyr Cys Tyr Phe Thr His Leu Gly Tyr Ile Ile Arg Tyr
        275                 280                 285

Pro Val Lys Arg Ile Ile Asp Ser Glu Val Val Phe Gly Glu Ala
    290                 295                 300

Val Lys Asp Lys Asn Trp Thr Val Tyr Leu Ile Lys Leu Ile Glu Pro
305                 310                 315                 320

Val Asn Ala Ile Asn Asp Arg Leu Glu Glu Ser Lys Tyr Val Glu Ser
                325                 330                 335

Lys Leu Val Asp Ile Cys Asp Arg Ile Val Phe Lys Ser Lys Lys Tyr
            340                 345                 350
```

```
Glu Gly Pro Phe Thr Thr Thr Ser Glu Val Val Asp Met Leu Ser Thr
        355                 360                 365
Tyr Leu Pro Lys Gln Pro Glu Gly Val Ile Leu Phe Tyr Ser Lys Gly
    370                 375                 380
Pro Lys Ser Asn Ile Asp Phe Lys Ile Lys Lys Glu Asn Thr Ile Asp
385                 390                 395                 400
Gln Thr Ala Asn Val Val Phe Arg Tyr Met Ser Ser Glu Pro Ile Ile
                405                 410                 415
Phe Gly Glu Ser Ser Ile Phe Val Glu Tyr Lys Lys Phe Ser Asn Asp
                420                 425                 430
Lys Gly Phe Pro Lys Glu Tyr Gly Ser Gly Lys Ile Val Leu Tyr Asn
        435                 440                 445
Gly Val Asn Tyr Leu Asn Asn Ile Tyr Cys Leu Glu Tyr Ile Asn Thr
        450                 455                 460
His Asn Glu Val Gly Ile Lys Ser Val Val Pro Ile Lys Phe Ile
465                 470                 475                 480
Ala Glu Phe Leu Val Asn Gly Glu Ile Leu Lys Pro Arg Ile Asp Lys
                485                 490                 495
Thr Met Lys Tyr Ile Asn Ser Glu Asp Tyr Gly Asn Gln His Asn
        500                 505                 510
Ile Ile Val Glu His Leu Arg Asp Gln Ser Ile Lys Ile Gly Asp Ile
        515                 520                 525
Phe Asn Glu Asp Lys Leu Ser Asp Val Gly His Gln Tyr Ala Asn Asn
530                 535                 540
Asp Lys Phe Arg Leu Asn Pro Glu Val Ser Tyr Phe Thr Asn Lys Arg
545                 550                 555                 560
Thr Arg Gly Pro Leu Gly Ile Leu Ser Asn Tyr Val Lys Thr Leu Leu
                565                 570                 575
Ile Ser Met Tyr Cys Ser Lys Thr Phe Leu Asp Asp Ser Asn Lys Arg
                580                 585                 590
Lys Val Leu Ala Ile Asp Phe Gly Asn Gly Ala Asp Leu Glu Lys Tyr
        595                 600                 605
Phe Tyr Gly Glu Ile Ala Leu Leu Val Ala Thr Asp Pro Asp Ala Asp
        610                 615                 620
Ala Ile Ala Arg Gly Asn Glu Arg Tyr Asn Lys Leu Asn Ser Gly Ile
625                 630                 635                 640
Lys Thr Lys Tyr Tyr Lys Phe Asp Tyr Ile Gln Glu Thr Ile Arg Ser
                645                 650                 655
Asp Thr Phe Val Ser Ser Val Arg Glu Val Phe Tyr Phe Gly Lys Phe
                660                 665                 670
Asn Ile Ile Asp Trp Gln Phe Ala Ile His Tyr Ser Phe His Pro Arg
                675                 680                 685
His Tyr Ala Thr Val Met Asn Asn Leu Ser Glu Leu Thr Ala Ser Gly
        690                 695                 700
Gly Lys Val Leu Ile Thr Thr Met Asp Gly Asp Lys Leu Ser Lys Leu
705                 710                 715                 720
Thr Asp Lys Lys Thr Phe Ile Ile His Lys Asn Leu Pro Ser Ser Glu
                725                 730                 735
Asn Tyr Met Ser Val Glu Lys Ile Ala Asp Asp Arg Ile Val Val Tyr
                740                 745                 750
Asn Pro Ser Thr Met Ser Thr Pro Met Thr Glu Tyr Ile Ile Lys Lys
        755                 760                 765
```

-continued

```
Asn Asp Ile Val Arg Val Phe Asn Glu Tyr Gly Phe Val Leu Val Asp
    770                 775                 780
Asn Val Asp Phe Ala Thr Ile Ile Glu Arg Ser Lys Lys Phe Ile Asn
785                 790                 795                 800
Gly Ala Ser Thr Met Glu Asp Arg Pro Ser Thr Arg Asn Phe Phe Glu
                805                 810                 815
Leu Asn Arg Gly Ala Ile Lys Cys Glu Gly Leu Asp Val Glu Asp Leu
                820                 825                 830
Leu Ser Tyr Tyr Val Val Tyr Val Phe Ser Lys Arg
            835                 840

<210> SEQ ID NO 7
<211> LENGTH: 287
<212> TYPE: PRT
<213> ORGANISM: Artificial Sequence
<220> FEATURE:
<223> OTHER INFORMATION: chemically synthesized polypeptide

<400> SEQUENCE: 7

Met Asp Glu Ile Val Lys Asn Ile Arg Glu Gly Thr His Val Leu Leu
1               5                   10                  15
Pro Phe Tyr Glu Thr Leu Pro Glu Leu Asn Leu Ser Leu Gly Lys Ser
            20                  25                  30
Pro Leu Pro Ser Leu Glu Tyr Gly Ala Asn Tyr Phe Leu Gln Ile Ser
        35                  40                  45
Arg Val Asn Asp Leu Asn Arg Met Pro Thr Asp Met Leu Lys Leu Phe
    50                  55                  60
Thr His Asp Ile Met Leu Pro Glu Ser Asp Leu Asp Lys Val Tyr Glu
65                  70                  75                  80
Ile Leu Lys Ile Asn Ser Val Lys Tyr Tyr Gly Arg Ser Thr Lys Ala
                85                  90                  95
Asp Ala Val Val Ala Asp Leu Ser Ala Arg Asn Lys Leu Phe Lys Arg
            100                 105                 110
Glu Arg Asp Ala Ile Lys Ser Asn Asn His Leu Thr Glu Asn Asn Leu
        115                 120                 125
Tyr Ile Ser Asp Tyr Lys Met Leu Thr Phe Asp Val Phe Arg Pro Leu
    130                 135                 140
Phe Asp Phe Val Asn Glu Lys Tyr Cys Ile Ile Lys Leu Pro Thr Leu
145                 150                 155                 160
Phe Gly Arg Gly Val Ile Asp Thr Met Arg Ile Tyr Cys Ser Leu Phe
                165                 170                 175
Lys Asn Val Arg Leu Leu Lys Cys Val Ser Asp Ser Trp Leu Lys Asp
            180                 185                 190
Ser Ala Ile Met Val Ala Ser Asp Val Cys Lys Lys Asn Leu Asp Leu
        195                 200                 205
Phe Met Ser His Val Lys Ser Val Thr Lys Ser Ser Trp Lys Asp
    210                 215                 220
Val Asn Ser Val Gln Phe Ser Ile Leu Asn Asn Pro Val Asp Thr Glu
225                 230                 235                 240
Phe Ile Asn Lys Phe Leu Glu Phe Ser Asn Arg Val Tyr Glu Ala Leu
                245                 250                 255
Tyr Tyr Val His Ser Leu Leu Tyr Ser Ser Met Thr Ser Asp Ser Lys
            260                 265                 270
Ser Ile Glu Asn Lys His Gln Arg Arg Leu Val Lys Leu Leu Leu
        275                 280                 285
```

<210> SEQ ID NO 8
<211> LENGTH: 946
<212> TYPE: PRT
<213> ORGANISM: Artificial Sequence
<220> FEATURE:
<223> OTHER INFORMATION: chemically synthesized polypeptide

<400> SEQUENCE: 8

```
Met Gly His His His His His His Gly Ser Leu Gln Glu Lys Pro
1               5                   10                  15

Lys Glu Gly Val Lys Thr Glu Asn Asp His Ile Asn Leu Lys Val Ala
            20                  25                  30

Gly Gln Asp Gly Ser Val Val Gln Phe Lys Ile Lys Arg His Thr Pro
        35                  40                  45

Leu Ser Lys Leu Met Lys Ala Tyr Cys Glu Arg Gln Gly Leu Ser Met
50                  55                  60

Arg Gln Ile Arg Phe Arg Phe Asp Gly Gln Pro Ile Asn Glu Thr Asp
65                  70                  75                  80

Thr Pro Ala Gln Leu Glu Met Glu Asp Glu Asp Thr Ile Asp Val Phe
                85                  90                  95

Gln Gln Gln Thr Gly Gly Met Asp Ala Asn Val Val Ser Ser Thr
            100                 105                 110

Ile Ala Thr Tyr Ile Asp Ala Leu Ala Lys Asn Ala Ser Glu Leu Glu
        115                 120                 125

Gln Arg Ser Thr Ala Tyr Glu Ile Asn Asn Glu Leu Glu Leu Val Phe
    130                 135                 140

Ile Lys Pro Pro Leu Ile Thr Leu Thr Asn Val Val Asn Ile Ser Thr
145                 150                 155                 160

Ile Gln Glu Ser Phe Ile Arg Phe Thr Val Thr Asn Lys Glu Gly Val
                165                 170                 175

Lys Ile Arg Thr Lys Ile Pro Leu Ser Lys Val His Gly Leu Asp Val
            180                 185                 190

Lys Asn Val Gln Leu Val Asp Ala Ile Asp Asn Ile Val Trp Glu Lys
        195                 200                 205

Lys Ser Leu Val Thr Glu Asn Arg Leu His Lys Glu Cys Leu Leu Arg
    210                 215                 220

Leu Ser Thr Glu Glu Arg His Ile Phe Leu Asp Tyr Lys Lys Tyr Gly
225                 230                 235                 240

Ser Ser Ile Arg Leu Glu Leu Val Asn Leu Ile Gln Ala Lys Thr Lys
                245                 250                 255

Asn Phe Thr Ile Asp Phe Lys Leu Lys Tyr Phe Leu Gly Ser Gly Ala
            260                 265                 270

Gln Ser Lys Ser Ser Leu Leu His Ala Ile Asn His Pro Lys Ser Arg
        275                 280                 285

Pro Asn Thr Ser Leu Glu Ile Glu Phe Thr Pro Arg Asp Asn Glu Thr
    290                 295                 300

Val Pro Tyr Asp Glu Leu Ile Lys Glu Leu Thr Leu Ser Arg His
305                 310                 315                 320

Ile Phe Met Ala Ser Pro Glu Asn Val Ile Leu Ser Pro Ile Asn
                325                 330                 335

Ala Pro Ile Lys Thr Phe Met Leu Pro Lys Gln Asp Ile Val Gly Leu
            340                 345                 350

Asp Leu Glu Asn Leu Tyr Ala Val Thr Lys Thr Asp Gly Ile Pro Ile
        355                 360                 365
```

```
Thr Ile Arg Val Thr Ser Asn Gly Leu Tyr Cys Tyr Phe Thr His Leu
    370                 375                 380
Gly Tyr Ile Ile Arg Tyr Pro Val Lys Arg Ile Ile Asp Ser Glu Val
385                 390                 395                 400
Val Val Phe Gly Glu Ala Val Lys Asp Lys Asn Trp Thr Val Tyr Leu
                405                 410                 415
Ile Lys Leu Ile Glu Pro Val Asn Ala Ile Asn Asp Arg Leu Glu Glu
            420                 425                 430
Ser Lys Tyr Val Glu Ser Lys Leu Val Asp Ile Cys Asp Arg Ile Val
        435                 440                 445
Phe Lys Ser Lys Lys Tyr Glu Gly Pro Phe Thr Thr Thr Ser Glu Val
450                 455                 460
Val Asp Met Leu Ser Thr Tyr Leu Pro Lys Gln Pro Glu Gly Val Ile
465                 470                 475                 480
Leu Phe Tyr Ser Lys Gly Pro Lys Ser Asn Ile Asp Phe Lys Ile Lys
                485                 490                 495
Lys Glu Asn Thr Ile Asp Gln Thr Ala Asn Val Val Phe Arg Tyr Met
            500                 505                 510
Ser Ser Glu Pro Ile Ile Phe Gly Glu Ser Ser Ile Phe Val Glu Tyr
        515                 520                 525
Lys Lys Phe Ser Asn Asp Lys Gly Phe Pro Lys Glu Tyr Gly Ser Gly
530                 535                 540
Lys Ile Val Leu Tyr Asn Gly Val Asn Tyr Leu Asn Asn Ile Tyr Cys
545                 550                 555                 560
Leu Glu Tyr Ile Asn Thr His Asn Glu Val Gly Ile Lys Ser Val Val
                565                 570                 575
Val Pro Ile Lys Phe Ile Ala Glu Phe Leu Val Asn Gly Glu Ile Leu
            580                 585                 590
Lys Pro Arg Ile Asp Lys Thr Met Lys Tyr Ile Asn Ser Glu Asp Tyr
        595                 600                 605
Tyr Gly Asn Gln His Asn Ile Ile Val Glu His Leu Arg Asp Gln Ser
610                 615                 620
Ile Lys Ile Gly Asp Ile Phe Asn Glu Asp Lys Leu Ser Asp Val Gly
625                 630                 635                 640
His Gln Tyr Ala Asn Asn Asp Lys Phe Arg Leu Asn Pro Glu Val Ser
                645                 650                 655
Tyr Phe Thr Asn Lys Arg Thr Arg Gly Pro Leu Gly Ile Leu Ser Asn
            660                 665                 670
Tyr Val Lys Thr Leu Leu Ile Ser Met Tyr Cys Ser Lys Thr Phe Leu
        675                 680                 685
Asp Asp Ser Asn Lys Arg Lys Val Leu Ala Ile Asp Phe Gly Asn Gly
690                 695                 700
Ala Asp Leu Glu Lys Tyr Phe Tyr Gly Glu Ile Ala Leu Leu Val Ala
705                 710                 715                 720
Thr Asp Pro Asp Ala Asp Ala Ile Ala Arg Gly Asn Glu Arg Tyr Asn
                725                 730                 735
Lys Leu Asn Ser Gly Ile Lys Thr Lys Tyr Tyr Lys Phe Asp Tyr Ile
            740                 745                 750
Gln Glu Thr Ile Arg Ser Asp Thr Phe Val Ser Val Arg Glu Val
        755                 760                 765
Phe Tyr Phe Gly Lys Phe Asn Ile Ile Asp Trp Gln Phe Ala Ile His
770                 775                 780
Tyr Ser Phe His Pro Arg His Tyr Ala Thr Val Met Asn Asn Leu Ser
```

```
                785                 790                 795                 800
Glu Leu Thr Ala Ser Gly Gly Lys Val Leu Ile Thr Thr Met Asp Gly
                    805                 810                 815

Asp Lys Leu Ser Lys Leu Thr Asp Lys Lys Thr Phe Ile Ile His Lys
                    820                 825                 830

Asn Leu Pro Ser Ser Glu Asn Tyr Met Ser Val Glu Lys Ile Ala Asp
                    835                 840                 845

Asp Arg Ile Val Val Tyr Asn Pro Ser Thr Met Ser Thr Pro Met Thr
        850                 855                 860

Glu Tyr Ile Ile Lys Lys Asn Asp Ile Val Arg Val Phe Asn Glu Tyr
865                 870                 875                 880

Gly Phe Val Leu Val Asp Asn Val Asp Phe Ala Thr Ile Ile Glu Arg
                    885                 890                 895

Ser Lys Lys Phe Ile Asn Gly Ala Ser Thr Met Glu Asp Arg Pro Ser
                    900                 905                 910

Thr Arg Asn Phe Phe Glu Leu Asn Arg Gly Ala Ile Lys Cys Glu Gly
                    915                 920                 925

Leu Asp Val Glu Asp Leu Leu Ser Tyr Tyr Val Val Tyr Val Phe Ser
        930                 935                 940

Lys Arg
945
```

MODIFICATION OF RNA-RELATED ENZYMES FOR ENHANCED PRODUCTION

RELATED APPLICATIONS

This application claims priority to U.S. Provisional Application Ser. No. 62/241,350, filed Oct. 14, 2015, the disclosure of which is hereby incorporated by reference.

SEQUENCE LISTING

The present specification makes reference to a Sequence Listing (submitted electronically as a .txt file named "SL_SHR-1187US" on Oct. 14, 2016. The .txt file was generated Oct. 14, 2016 and is 28,402 bytes in size. The entire contents of the Sequence Listing are herein incorporated by reference.

BACKGROUND

Messenger RNA ("mRNA") therapy is becoming an increasingly important approach for the treatment of a variety of diseases. Effective mRNA therapy requires effective delivery of the mRNA to the patient and efficient production of the protein encoded by the mRNA within the patient's body. To optimize mRNA delivery and protein production in vivo, a proper cap are typically required at the 5' end of the construct, which protects the mRNA from degradation and facilitates successful protein translation. Therefore, the large-scale production of enzymes capable of capping mRNA is particularly important for producing mRNA for therapeutic applications.

SUMMARY OF THE INVENTION

The present invention provides improved methods for effective production of enzymes capable of capping mRNA. The present invention is, in part, based on the surprising discovery that modifying a guanylyl transferase (GT) with a SUMO tag makes it possible to produce GT on the large scale needed for producing capped mRNA for therapeutic applications.

Thus, in one aspect, the present invention provides methods of producing a capped RNA or RNA analog oligonucleotide, wherein a fusion protein facilitates the steps of transferring and methylating a guanylyl molecule to the 5' end of the RNA or RNA analog oligonucleotide.

In some embodiments, the fusion protein comprises a guanylyl transferase and a small ubiquitin-like molecule (SUMO) protein. In some embodiments, the guanylyl transferase comprises SEQ ID NO: 6 and SEQ ID NO: 7 and the SUMO protein comprises SEQ ID NO: 1. In some embodiments, the fusion protein comprises SEQ ID NO: 8 and SEQ ID NO: 7.

In some embodiments, the one end of the RNA or RNA analog oligonucleotide is the 5' end.

In some embodiments, the fusion protein has comparable phosphatase activity, guanylyl transferase activity and methylation activity relative to a wild-type guanylyl transferase protein.

In another aspect, the present invention provides fusion proteins, wherein a fusion protein comprises guanylyl transferase and a small ubiquitin-like molecule (SUMO) protein.

In some embodiments, the guanylyl transferase comprises SEQ ID NO: 6 and SEQ ID NO: 7 and the SUMO protein comprises SEQ ID NO: 1. In some embodiments, the guanylyl transferase comprises a large subunit and a small subunit. In some embodiments, the SUMO protein is covalently linked and co-expressed with the large subunit. In some embodiments, the fusion protein has comparable phosphatase activity, guanylyl transferase activity and methylation activity relative to a wild-type guanylyl transferase protein.

In another aspect, the present invention provides vectors encoding a fusion protein comprising guanylyl transferase protein and a small ubiquitin-like molecule (SUMO) protein.

In some embodiments, the vector comprises SEQ ID NO: 5 and SEQ ID NO: 2. In some embodiments, the vector comprises SEQ ID NO: 5, SEQ ID NO: 2, and SEQ ID NO: 3. In some embodiments, the vector comprises SEQ ID NO: 4 and SEQ ID NO: 3.

In another aspect, the present invention provides methods to produce a guanylyl transferase by fermentation, comprising: a) culturing in a fermentation medium a microorganism that is transformed with at least one recombinant nucleic acid molecule comprising a nucleic acid sequence encoding a guanylyl transferase that has an amino acid sequence that is at least 90% identical SEQ ID NO: 6 and SEQ ID NO: 7; and b) collecting a product produced from the step of culturing.

In some embodiments, the guanylyl transferase comprises a guanylyl transferase fusion protein. In some embodiments, the guanylyl transferase fusion protein has comparable phosphatase activity, guanylyl transferase activity and methylation activity relative to a wild-type guanylyl transferase protein. In some embodiments, the guanylyl transferase fusion protein comprises a small ubiquitin-like molecule (SUMO) protein. In some embodiments, the guanylyl transferase fusion protein comprises SEQ ID NO: 8.

In some embodiments, the SUMO protein is bound to the guanylyl transferase by a covalent link. In some embodiments, the covalent link is between the SUMO protein and a large subunit of the guanylyl transferase.

In some embodiments, the fermentation medium is selected from the group consisting of Terrific Broth, Cinnabar, 2xYT and LB. In some embodiments, the microorganism is a bacterium.

In some embodiments, the nucleic acid sequence encoding the guanylyl transferase is at least 90% identical to SEQ ID NO: 2 and SEQ ID NO: 3.

In some embodiments, the recombinant nucleic acid molecule further comprises a nucleic acid sequence encoding a small ubiquitin-like molecule (SUMO) protein. In some embodiments, the nucleic acid sequence encoding a small ubiquitin-like molecule (SUMO) protein is at least 90% identical to SEQ ID NO: 5.

In some embodiments, the product is a guanylyl transferase. In some embodiments, the product is a guanylyl transferase comprises a guanylyl transferase fusion protein. In some embodiments, the guanylyl transferase fusion protein further comprises a small ubiquitin-like molecule (SUMO) protein.

BRIEF DESCRIPTION OF THE DRAWING

The drawings are for illustration purposes and are in no way limiting.

DEFINITIONS

Figure 1A:
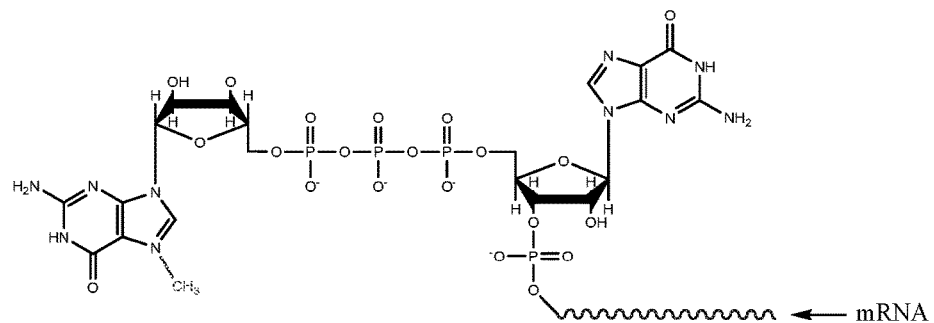
FIGS. 1A and 1B are diagrams of exemplary mRNA capped structures present in various embodiments of the invention.

In order for the present invention to be more readily understood, certain terms are first defined. Additional definitions for the following terms and other terms are set forth throughout the specification.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Batch culture: As used herein, the term "batch culture" refers to a method of culturing cells in which all the components that will ultimately be used in culturing the cells, including the medium (see definition of "medium" below) as well as the cells themselves, are provided at the beginning of the culturing process. Thus, a batch culture typically refers to a culture allowed to progress from inoculation to conclusion without refeeding the cultured cells with fresh medium. A batch culture is typically stopped at some point and the cells and/or components in the medium are harvested and optionally purified.

Biologically active: As used herein, the phrase "biologically active" refers to a characteristic of any substance that has activity in a biological system (e.g., cell culture, organism, etc.). For instance, a substance that, when administered to an organism, has a biological effect on that organism, is considered to be biologically active. Biological activity can also be determined by in vitro assays (for example, in vitro enzymatic assays such as sulfate release assays). In particular embodiments, where a protein or polypeptide is biologically active, a portion of that protein or polypeptide that shares at least one biological activity of the protein or polypeptide is typically referred to as a "biologically active" portion. In some embodiments, a protein is produced and/or purified from a cell culture system, which displays biologically activity when administered to a subject. In some embodiments, a protein requires further processing in order to become biologically active. In some embodiments, a protein requires posttranslational modification such as, but is not limited to, glycosylation (e.g., sialyation), farnysylation, cleavage, folding, formylglycine conversion and combinations thereof, in order to become biologically active. In some embodiments, a protein produced as a proform (i.e. immature form), may require additional modification to become biologically active.

Bioreactor: As used herein, the term "bioreactor" refers to a vessel used for the growth of a host cell culture. A bioreactor can be of any size so long as it is useful for the culturing of mammalian cells. Typically, a bioreactor will be at least 1 liter and may be 10, 100, 250, 500, 1000, 2500, 5000, 8000, 10,000, 12,0000 liters or more, or any volume in between. Internal conditions of a bioreactor, including, but not limited to pH, osmolarity, CO2 saturation, 02 saturation, temperature and combinations thereof, are typically controlled during the culturing period. A bioreactor can be composed of any material that suitable for holding cells in media under the culture conditions of the present invention, including glass, plastic or metal. In some embodiments, a bioreactor may be used for performing animal cell culture. In some embodiments, a bioreactor may be used for performing mammalian cell culture. In some embodiments, a bioreactor may be used with cells and/or cell lines derived from such organisms as, but not limited to, mammalian cell, insect cells, bacterial cells, yeast cells and human cells. In some embodiments, a bioreactor is used for large-scale cell culture production and is typically at least 100 liters and may be 200, 500, 1000, 2500, 5000, 8000, 10,000, 12,0000 liters or more, or any volume in between. One of ordinary skill in the art will be aware of and will be able to choose suitable bioreactors for use in practicing the present invention.

Cell density: As used herein, the term "cell density" refers to that number of cells present in a given volume of medium.

Cell culture or culture: As used herein, these terms refer to a cell population that is gown in a medium under conditions suitable to survival and/or growth of the cell population. As will be clear to those of ordinary skill in the art, these terms as used herein may refer to the combination comprising the cell population and the medium in which the population is grown.

Cultivation: As used herein, the term "cultivation" or grammatical equivalents refers to a process of maintaining cells under conditions favoring growth or survival. The terms "cultivation" and "cell culture" or any synonyms are used inter-changeably in this application.

Culture vessel: As used herein, the term "culture vessel" refers to any container that can provide an aseptic environment for culturing cells. Exemplary culture vessels include, but are not limited to, glass, plastic, or metal containers.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Fed-batch culture: As used herein, the term "fed-batch culture" refers to a method of culturing cells in which additional components are provided to the culture at some time subsequent to the beginning of the culture process. The provided components typically comprise nutritional supplements for the cells which have been depleted during the culturing process. A fed-batch culture is typically stopped at some point and the cells and/or components in the medium are harvested and optionally purified.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Various other sequence alignment programs are available and can be used to determine sequence identity such as, for example, Clustal.

Integrated Viable Cell Density: As used herein, the term "integrated viable cell density" refers to the average density of viable cells over the course of the culture multiplied by the amount of time the culture has run. Assuming the amount of polypeptide and/or protein produced is proportional to the number of viable cells present over the course of the culture, integrated viable cell density is a useful tool for estimating the amount of polypeptide and/or protein produced over the course of the culture.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.)

Medium: As used herein, the term "medium" refer to a solution containing nutrients which nourish growing cells. Typically, these solutions provide essential and nonessential amino acids, vitamins, energy sources, lipids, and trace elements required by the cell for minimal growth and/or survival. The solution may also contain components that enhance growth and/or survival above the minimal rate, including hormones and growth factors. In some embodiments, medium is formulated to a pH and salt concentration optimal for cell survival and proliferation. In some embodiments, medium may be a "chemically defined medium"—a serum-free media that contains no proteins, hydrolysates or components of unknown composition. In some embodiment, chemically defined medium is free of animal-derived components and all components within the medium have a known chemical structure. In some embodiments, medium may be a "serum based medium"—a medium that has been supplemented with animal derived components such as, but not limited to, fetal calf serum, horse serum, goat serum, donkey serum and/or combinations thereof.

Nucleic acid: As used herein, the term "nucleic acid," in its broadest sense, refers to a compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Perfusion process: As used herein, the term "perfusion process" refers to a method of culturing cells in which additional components are provided continuously or semi-continuously to the culture subsequent to the beginning of the culture process. The provided components typically comprise nutritional supplements for the cells which have been depleted during the culturing process. A portion of the cells and/or components in the medium are typically harvested on a continuous or semi-continuous basis and are optionally purified. Typically, a cell culture process involving a perfusion process is referred to as "perfusion culture." Typically, nutritional supplements are provided in a fresh medium during a perfusion process. In some embodiments, a fresh medium may be identical or similar to the base medium used in the cell culture process. In some embodiments, a fresh medium may be different than the base medium but containing desired nutritional supplements. In some embodiments, a fresh medium is a chemically-defined medium.

Seeding: As used herein, the term "seeding" refers to the process of providing a cell culture to a bioreactor or another vessel for large scale cell culture production. In some embodiments a "seed culture" is used, in which the cells have been propagated in a smaller cell culture vessel, i.e. Tissue-culture flask, Tissue-culture plate, Tissue-culture roller bottle, etc., prior to seeding. Alternatively, in some embodiments, the cells may have been frozen and thawed immediately prior to providing them to the bioreactor or vessel. The term refers to any number of cells, including a single cell.

Subject: As used herein, the term "subject" means any mammal, including humans. In certain embodiments of the present invention the subject is an adult, an adolescent or an infant. Also contemplated by the present invention are the administration of the pharmaceutical compositions and/or performance of the methods of treatment in-utero.

Vector: As used herein, "vector" refers to a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

Viable cell density: As used herein, the term "viable cell density" refers to the number of living cells per unit volume.

DETAILED DESCRIPTION

The present invention provides, among other things, methods and compositions for large-scale production of capped mRNA using SUMO-Guanylyl Transferase fusion protein.

Various aspects of the invention are described in further detail in the following subsections. The use of subsections is not meant to limit the invention. Each subsection may apply to any aspect of the invention. In this application, the use of "or" means "and/or" unless stated otherwise.

SUMO-Guanylyl Transferase Fusion Protein

Small Ubiquitin-Like Modifier (SUMO)

As used herein, a SUMO tag is any protein or a portion of a protein that can substitute for at least partial activity of a SUMO protein.

SUMO proteins are small proteins that are covalently attached to and detached from other proteins in order to modify the functions of those proteins. The modification of a protein with a SUMO protein is a post-translational modification involved in various cellular processes such as nuclear-cytosolic transport, transcriptional regulation, apoptosis, protein stability, response to stress and progression through the cell cycle. There are at least 4 SUMO paralogs in vertebrates, designated SUMO-1, SUMO-2, SUMO-3, and SUMO-4. SUMO-2 and SUMO-3 are structurally and functionally very similar and are distinct from SUMO-1. The amino acid sequence (SEQ ID NO: 1) spans amino acids 3-92 of a typical wild-type or naturally occurring SUMO-3 protein is shown in Table 1. In addition, a codon optimized DNA sequence encoding the SUMO-3 protein is also provided in Table 1, as SEQ ID NO: 5.

TABLE 1

Small Ubiquitin-like Modifier

| | |
|---|---|
| SUMO-3 Protein sequence | EEKPKEGVKTENDHINLKVAGQDGSVVQFKIKRH TPLSKLMKAYCERQGLSMRQIRFRFDGQPINETD TPAQLEMEDEDTIDVFQQQTGG (SEQ ID NO: 1) |
| SUMO-3 DNA sequence | GAAGAGAAACCGAAAGAGGGCGTTAAGACCGAGA ATGACCACATTAACCTGAAGGTCGCTGGTCAAGA TGGCAGCGTGGTGCAGTTTAAGATCAAGCGTCAC ACGCCGTTGAGCAAGCTGATGAAGGCTTACTGCG AGCGTCAGGGTCTGAGCATGCGTCAGATCCGCTT TCGTTTCGATGGCCAGCCGATCAATGAGACTGAC ACCCCAGCGCAACTGG (SEQ ID NO: 5) |

Thus, in some embodiments, a SUMO protein is a human SUMO-3 protein (SEQ ID NO: 1). In some embodiments, the SUMO protein may be another SUMO paralog, such as SUMO-1, SUMO-2 or SUMO-4. In some embodiments, a suitable replacement protein may be a homologue or an analogue of human SUMO-3 protein. For example, a homologue or an analogue of SUMO-3 protein may be a modified SUMO-3 protein containing one or more amino acid substitutions, deletions, and/or insertions as compared to a wild-type or naturally-occurring SUMO-3 protein (e.g. SEQ ID NO: 1), while retaining substantial SUMO-3 protein activity. Thus, in some embodiments, an enzyme suitable for the present invention is substantially homologous to a wild-type or naturally-occurring SUMO-3 protein (SEQ ID NO: 1). In some embodiments, an enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 1. In some embodiments, an enzyme suitable for the present invention is substantially identical to a wild-type or naturally-occurring SUMO-3 protein (SEQ ID NO: 1). In some embodiments, a protein suitable for the present invention contains a fragment or a portion of a SUMO protein. In some embodiments, the SUMO protein comprises human SUMO-1, human SUMO-2, human SUMO-3, any one of *Arabidopsis Zhalania* SUMO-1 through SUMO-8, tomato SUMO, any one of *Xenopus laevis* SUMO-1 through SUMO-3, *Drosophila melanogasler* Smt3, *Caenorhabdilis elegans* SMO-1, *Schizosaccharomyces pombe* Pmt3, malarial parasite *Plasmodium falciparum* SUMO, mold *Aspergillus nidulans* SUMO, an equivalent thereof, a homologue thereof, or a combination thereof.

In some embodiments, the SUMO protein is encoded by a nucleic acid derived from an organism selected from the group consisting of human, mouse, insect, plant, yeast, and other eukaryotic organisms. In some embodiments, the SUMO protein is encoded by a nucleic acid derived from an organism selected from the group consisting of *Homo sapiens, Arabidopsis Zhalania,* tomato, *Xenopus laevis, Drosophila melanogasler, Caenorhabdilis elegans, Schizosaccharomyces pombe, Plasmo diumfalciparum,* or *Aspergillus nidulans.* In some embodiments, a nucleic acid suitable for the present invention has an sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 5. In some embodiments, a nucleic acid suitable for the present invention is substantially identical to a nucleic acid encoding a wild-type or naturally-occurring SUMO-3 protein (SEQ ID NO: 5).

Guanylyl Transferase (GT)

As used herein, a GT protein is any protein or portion of a protein that can substitute for at least partial activity of naturally-occurring Guanylyl Transferase (GT) protein. As used herein, the terms "a GT protein" and "a GT enzyme" and grammatical equivalents are used interchangeably.

GT is an enzyme derived from the Vaccinia Virus system that facilitates the transfer and methylation of a guanylyl molecule to the 5' end of a messenger RNA molecule. This process, known as mRNA capping, is highly regulated and important for the creation of stable and mature mRNA able to undergo translation during protein synthesis. The GT enzyme comprises a heterodimer that includes a "large subunit" (D1, about 97 kDa) and a "small subunit (D12, about 33 kDa). GT provides three enzymatic functions: phosphatase activity (cleavage of the nascent 5' triphosphate of mRNA to a diphosphate), guanylyl transferase activity (incorporation of a GTP molecule to the 5' end of the mRNA moiety) and methylation activity (incorporation of a methyl group at the $N^7$ position of the guanylyl base). The amino acid sequence of the large subunit (SEQ ID NO: 6) and small subunit (SEQ ID NO: 7) of a typical wild-type or naturally occurring GT protein are shown in Table 2. In addition, codon optimized DNA sequences encoding the large and small subunits of GT are also provided in Table 2, as SEQ ID NO: 2 and SEQ ID NO: 3, respectively.

TABLE 2

| Guanylyl Transferase | |
|---|---|
| Large subunit (Protein sequence) | MDANVVSSSTIATYIDALAKNASELEQRSTAYEINNELELVFIKPPL ITLTNVVNISTIQESFIRFTVTNKEGVKIRTKIPLSKVHGLDVKNVQL VDAIDNIVWEKKSLVTENRLHKECLLRLSTEERHIFLDYKKYGSSI RLELVNLIQAKTKNFTIDFKLKYFLGSGAQSKSSLLHAINHPKSRPN TSLEIEFTPRDNETVPYDELIKELTTLSRHIFMASPENVILSPPINAPI KTFMLPKQDIVGLDLENLYAVTKTDGIPITIRVTSNGLYCYFTHLG YIIRYPVKRIIDSEVVVFGEAVKDKNWTVYLIKLIEPVNAINDRLEE SKYVESKLVDICDRIVFKSKKYEGPFTTTSEVVDMLSTYLPKQPEG VILFYSKGPKSNIDFKIKKENTIDQTANVVFRYMSSEPIIFGESSIFVE YKKFSNDKGFPKEYGSGKIVLYNGVNYLNNIYCLEYINTHNEVGI KSVVVPIKFIAEFLVNGEILKPRIDKTMKYINSEDYYGNQHNIIVEH LRDQSIKIGDIFNEDKLSDVGHQYANNDKFRLNPEVSYFTNKRTRG PLGILSNYVKTLLISMYCSKTFLDDSNKRKVLAIDFGNGADLEKYF YGEIALLVATDPDADAIARGNERYNKLNSGIKTKYYKFDYIQETIR SDTFVSSVREVFYFGKFNIIDWQFAIHYSFHPRHYATVMNNLSELT ASGGKVLITTMDGDKLSKLTDKKTFIIHKNLPSSENYMSVEKIADD RIVVYNPSTMSTPMTEYIIKKNDIVRVFNEYGFVLVDNVDFATIIER SKKFINGASTMEDRPSTRNFFELNRGAIKCEGLDVEDLLSYYVVY VFSKR (SEQ ID NO: 6) |
| Small subunit (Protein sequence) | MDEIVKNIREGTHVLLPFYETLPELNLSLGKSPLPSLEYGANYFLQI SRVNDLNRMPTDMLKLFTHDIMLPESDLDKVYEILKINSVKYYGR STKADAVVADLSARNKLFKRERDAIKSNNHLTENNLYISDYKMLT FDVFRPLFDFVNEKYCIIKLPTLFGRGVIDTMRIYCSLFKNVRLLKC VSDSWLKDSAIMVASDVCKKNLDLFMSHVKSVTKSSSWKDVNSV QFSILNNPVDTEFINKFLEFSNRVYEALYYVHSLLYSSMTSDSKSIE NKHQRRLVKLLL (SEQ ID NO: 7) |
| Large subunit (DNA sequence) | AGATGGAAGATGAAGATACCATCGACGTCTTTCAGCAACAGAC CGGTGGTATGGATGCTAACGTCGTTAGCAGCAGCACCATTGCG ACTTACATTGATGCACTGGCCAAAAACGCATCTGAGCTTGAGC AGCGCAGCACCGCCTACGAGATCAATAACGAATTGGAGCTGGT TTTCATTAAACCGCCGCTGATCACGCTGACGAACGTCGTGAAC ATTAGCACGATTCAAGAGAGCTTTATTCGTTTCACCGTTACCAA TAAAGAAGGCGTGAAGATCCGTACCAAGATTCCGCTGAGCAAA GTGCATGGTCTGGACGTGAAAAATGTGCAGCTGGTTGATGCGA TCGATAACATCGTGTGGGAGAAGAAATCTTTGGTCACGGAAAA TCGTCTGCACAAGGAATGTCTGCTGCGTCTGTCAACCGAAGAA CGCCACATCTTCCTGGACTACAAGAAGTATGGTTCCAGCATCCG TCTGGAACTGGTGAACCTGATTCAGGCAAAGACCAAGAACTTC ACCATTGACTTCAAACTGAAGTATTTCCTGGGCTCTGGTGCACA GAGCAAATCCAGCTTGTTGCACGCGATTAACCATCCGAAGAGC CGTCCGAATACGAGCCTGGAGATCGAATTCACGCCGCGTGATA ACGAAACCGTTCCGTACGATGAGCTGATTAAAGAACTGACGAC GTTGAGCCGCCACATCTTTATGGCCAGCCCGGAAAACGTGATC CTTAGCCGCCTATCAATGCGCCGATTAAAACCTTTATGTTACC GAAACAAGACATTGTGGGTCTGGACCTGGAAAACCTGTACGCG GTCACCAAAACGGACGGCATTCCGATCACGATTCGTGTTACCA GCAATGGTCTGTACTGCTATTTCACTCATTTGGGCTATATCATT CGTTATCCGGTGAAACGCATCATTGATTCTGAGGTTGTCGTTTT CGGCGAAGCAGTCAAGGACAAGAATTGGACTGTGTACCTGATC AAATTGATTGAACCGGTTAACGCCATCAATGACCGCCTGGAAG |

TABLE 2 -continued

Guanylyl Transferase

|  |  |
|---|---|
|  | AGTCGAAATATGTTGAAAGCAAACTGGTGGATATTTGTGATCG<br>TATCGTGTTCAAGAGCAAGAAATATGAAGGCCCGTTCACCACG<br>ACCAGCGAAGTTGTTGACATGCTGAGCACCTATCTGCCGAAAC<br>AACCTGAGGGTGTGATTCTGTTTTACTCCAAGGGTCCGAAGAG<br>CAACATTGATTTCAAAATCAAGAAAGAGAATACCATTGATCAG<br>ACCGCCAACGTTGTGTTCCGCTATATGTCCAGCGAGCCTATCAT<br>TTTCGGTGAGTCGAGCATCTTTGTTGAATACAAAAAGTTTAGCA<br>ACGATAAGGGTTTTCCGAAAGAATACGGTTCCGGTAAGATTGT<br>GTTGTACAACGGCGTCAATTATCTGAACAACATCTACTGTCTGG<br>AGTACATCAATACCCATAACGAAGTTGGCATTAAGTCTGTTGTC<br>GTCCCGATCAAATTCATCGCGGAGTTCCTGGTTAACGGTGAGAT<br>TCTGAAGCCGCGTATTGATAAAACTATGAAATACATTAACTCC<br>GAAGATTACTACGGTAATCAGCATAACATCATCGTCGAGCACT<br>TGCGTGATCAAAGCATTAAGATCGGTGACATCTTTAACGAAGA<br>TAAGCTGAGCGATGTAGGCCACCAGTATGCGAACAATGACAAA<br>TTTCGCCTGAATCCGGAAGTCAGCTACTTTACGAATAAGCGCAC<br>CCGTGGTCCACTGGGTATCCTGAGCAATTATGTTAAAACCCTGT<br>TGATTTCCATGTACTGCTCCAAAACGTTCCTGGACGACAGCAAC<br>AAGCGCAAAGTTCTGGCGATCGACTTCGGTAATGGTGCCGATC<br>TGGAGAAGTACTTTTATGGTGAGATCGCATTGCTGGTTGCTACC<br>GACCCGGATGCAGATGCGATCGCCCGTGGCAACGAGCGTTACA<br>ATAAGCTGAATAGCGGTATCAAGACCAAATACTACAAATTCGA<br>CTATATTCAAGAGACGATCCGCTCGGACACCTTTGTATCCAGCG<br>TGCGTGAGGTGTTTTACTTCGGTAAATTCAACATCATTGACTGG<br>CAATTCGCCATTCACTATAGCTTTCACCCACGCCACTATGCGAC<br>GGTCATGAACAACCTGTCTGAGCTGACCGCGAGCGGCGGTAAA<br>GTTCTGATCACCACGATGGACGGTGACAAGCTGTCTAAACTGA<br>CCGACAAAAAGACCTTCATTATTCACAAAAATCTCCCGTCGAG<br>CGAGAATTACATGTCCGTCGAAAAGATTGCGGACGACCGTATT<br>GTTGTCTACAACCCGAGCACTATGTCGACCCCAATGACCGAGT<br>ATATCATCAAAAAGAATGACATTGTGCGTGTCTTTAATGAATAC<br>GGTTTTGTGCTGGTCGACAACGTCGATTTTGCGACCATCATCGA<br>GAGAAGCAAGAAATTCATTAATGGCGCTTCTACGATGGAAGAT<br>CGCCCGAGCACGCGTAACTTCTTTGAGCTGAATCGTGGCGCGA<br>TTAAGTGCGAGGGCCTGGACGTCGAGGATCTGCTGTCGTATTA<br>CGTGGTTTATGTGTTTAGCAAACGTTAATGA (SEQ ID NO: 2) |
| Small subunit<br>(DNA sequence) | ATGGACGAAATTGTCAAGAATATCCGTGAAGGTACCCACGTTT<br>TACTGCCATTCTACGAGACGCTGCCGGAACTGAACCTGAGCCT<br>GGGTAAAAGCCCTCTGCCGAGCCTGGAGTATGGTGCGAACTAT<br>TTTCTGCAGATTTCCCGTGTAAACGATTTGAACCGCATGCCGAC<br>GGACATGCTGAAACTGTTCACCCACGACATCATGCTGCCGGAA<br>TCTGATCTGGATAAAGTTTACGAGATCTTGAAAATCAATTCAGT<br>GAAGTACTATGCCGTAGCACCAAGGCCGATGCGGTGGTCGCA<br>GACCTGAGCGCGCGTAACAAACTGTTTAAACGTGAACGTGACG<br>CAATTAAGAGCAATAACCATCTGACCGAGAACAATTTGTACAT<br>CAGCGACTACAAGATGTTGACTTTTGACGTGTTTCGTCCGCTGT<br>TCGACTTTGTTAATGAGAAATACTGCATTATCAAGCTGCCGACG<br>TTGTTTGGTCGCGGCGTCATTGATACGATGCGCATTTACTGCTC<br>TCTCTTCAAGAATGTGCGCCTGCTGAAGTGTGTCTCCGACAGCT<br>GGCTGAAAGATAGCGCTATTATGGTTGCGAGCGACGTGTGTAA<br>AAAGAACCTGGATCTGTTCATGAGCCACGTGAAGAGCGTTACC<br>AAAAGCAGCAGCTGGAAAGACGTTAACAGCGTCCAGTTCTCCA<br>TTCTGAATAACCCGGTCGATACCGAGTTTATCAACAAGTTCCTT<br>GAATTCAGCAATCGCGTTTATGAGGCCCTGTATTACGTTCATAG<br>CCTGCTGTATAGCTCCATGACCTCTGATAGCAAATCGATCGAGA<br>ATAAACACCAACGTCGTCTGGTGAAACTGCTGCTGTAATGA<br>(SEQ ID NO: 3) |

Thus, in some embodiments, a GT enzyme is a heterodimer comprising large and small subunits (SEQ ID NO: 6 and SEQ ID NO: 7, respectively). In some embodiments, the GT enzyme of the invention may be a homologue or analogue of one or the other of the GT large and small subunits. For example, a homologue or analogue of GT protein may be a modified GT protein containing one or more amino acid substitutions, deletions, and/or insertions as compared to SEQ ID NO: 6 and/or SEQ ID NO: 7, while retaining substantial GT protein activity. Thus, in some embodiments, an enzyme suitable for the present invention is substantially homologous to the GT protein large and small subunits (SEQ ID NO: 6 and SEQ ID NO: 7). In some embodiments, an enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 6. In some embodiments, an enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 7. In some embodiments, an enzyme suitable for the present invention is substantially identical to the large and small subunits of GT (SEQ ID NO: 6 and SEQ ID NO: 7). In some embodiments, an enzyme suitable for the present invention contains a fragment or a portion of a GT protein.

In some embodiments, the GT protein is encoded by a nucleic acid derived from an virus selected from the group consisting of Vaccinia virus, Rabbitpox virus, Cowpox virus, Taterapox virus, Monkeypox virus, Variola major virus, Camelpox virus, Ectromelia virus, Variola minor virus, Orthopox virus, Raccoonpox virus, Skunkpox virus, Volepox virus, Yoka pox virus, Swinepox virus, Yaba monkey tumor virus, Deerpox virus, Myxoma virus, Tanapox virus, Goatpox virus, Rabbit fibroma virus, Lumpy skin disease virus, Sheeppox virus, Eptesipox virus, Squirrelpox virus, Molluscum contagiosum virus, Cotia virus, Orf virus, Bovine popular stomatitis virus, Pseudocowpox virus, Canarypox virus, Pidgeonpox virus, Penguinpox virus, and Fowlpox virus. In some embodiments, nucleic acids suitable for the present invention have a sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 2. In some embodiments, nucleic acids suitable for the present invention have a sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 3. In some embodiments, nucleic acids suitable for the present invention are substantially identical to a nucleic acid encoding a GT protein (SEQ ID NO: 2 and SEQ ID NO: 3).

SUMO-GT Fusion

As used herein, a SUMO-GT fusion protein is any protein or portion of a protein that comprises a SUMO protein covalently linked to a Guanylyl Transferase (GT) protein, wherein the fusion protein can substitute for at least partial activity of naturally-occurring Guanylyl Transferase (GT) protein. As used herein, the terms "a SUMO-GT fusion protein" and "a SUMO-GT fusion enzyme" and grammatical equivalents are used interchangeably. An exemplary amino acid sequence of the fusion of SUMO and the GT large subunit (SEQ ID NO: 8) are shown in Table 3. In addition, an exemplary DNA sequence encoding the fusion of SUMO and the GT large subunit is also provided in Table 3, as SEQ ID NO: 4.

TABLE 3

| SUMO-GT Fusion | |
|---|---|
| SUMO-GT large subunit DNA construct with His tag and linker | ATGGGCCATCATCATCACCATCACGGCAGCCTGCAAGAAGAGA<br>AACCGAAAGAGGGCGTTAAGACCGAGAATGACCACATTAACCT<br>GAAGGTCGCTGGTCAAGATGGCAGCGTGGTGCAGTTTAAGATC<br>AAGCGTCACACGCCGTTGAGCAAGCTGATGAAGGCTTACTGCG<br>AGCGTCAGGGTCTGAGCATGCGTCAGATCCGCTTTCGTTTCGAT<br>GGCCAGCCGATCAATGAGACTGACACCCCAGCGCAACTGGAGA<br>TGGAAGATGAAGATACCATCGACGTCTTTCAGCAACAGACCGG<br>TGGTATGGATGCTAACGTCGTTAGCAGCAGCACCATTGCGACTT<br>ACATTGATGCACTGGCCAAAAACGCATCTGAGCTTGAGCAGCG<br>CAGCACCGCCTACGAGATCAATAACGAATTGGAGCTGGTTTTC<br>ATTAAACCGCCGCTGATCACGCTGACGAACGTCGTGAACATTA<br>GCACGATTCAAGAGAGCTTTATTCGTTTCACCGTTACCAATAAA<br>GAAGGCGTGAAGATCCGTACCAAGATTCCGCTGAGCAAAGTGC<br>ATGGTCTGGACGTGAAAAATGTGCAGCTGGTTGATGCGATCGA<br>TAACATCGTGTGGGAGAAGAAATCTTTGGTCACGGAAAATCGT<br>CTGCACAAGGAATGTCTGCTGCGTCTGTCAACCGAAGAACGCC<br>ACATCTTCCTGGACTACAAGAAGTATGGTTCCAGCATCCGTCTG<br>GAACTGGTGAACCTGATTCAGGCAAAGACCAAGAACTTCACCA<br>TTGACTTCAAACTGAAGTATTTCCTGGGCTCTGGTGCACAGAGC<br>AAATCCAGCTTGTTGCACGCGATTAACCATCCGAAGAGCCGTC<br>CGAATACGAGCCTGGAGATCGAATTCACGCCGCGTGATAACGA<br>AACCGTTCCGTACGATGAGCTGATTAAAGAACTGACGACGTTG<br>AGCCGCCACATCTTTATGGCCAGCCCGGAAAACGTGATCCTTA<br>GCCCGCCTATCAATGCGCCGATTAAAACCTTTATGTTACCGAAA<br>CAAGACATTGTGGGTCTGGACCTGGAAAACCTGTACGCGGTCA<br>CCAAAACGGACGGCATTCCGATCACGATTCGTGTTACCAGCAA<br>TGGTCTGTACTGCTATTTCACTCATTTGGGCTATATCATTCGTTA<br>TCCGGTGAAACGCATCATTGATTCTGAGGTTGTCGTTTTCGGCG<br>AAGCAGTCAAGGACAAGAATTGGACTGTGTACCTGATCAAATT<br>GATTGAACCGGTTAACGCCATCAATGACCGCCTGGAAGAGTCG<br>AAATATGTTGAAAGCAAACTGGTGGATATTTGTGATCGTATCGT<br>GTTCAAGAGCAAGAAATATGAAGGCCCGTTCACCACGACCAGC<br>GAAGTTGTTGACATGCTGAGCACCTATCTGCCGAAACAACCTG<br>AGGGTGTGATTCTGTTTTACTCCAAGGGTCCGAAGAGCAACATT<br>GATTTCAAAATCAAGAAAGAGAATACCATTGATCAGACCGCCA<br>ACGTTGTGTTCCGCTATATGTCCAGCGAGCCTATCATTTTCGGT<br>GAGTCGAGCATCTTTGTTGAATACAAAAAGTTTAGCAACGATA<br>AGGGTTTTCCGAAAGAATACGGTTCCGGTAAGATTGTGTTGTAC<br>AACGGCGTCAATTATCTGAACAACATCTACTGTCTGGAGTACAT<br>CAATACCCATAACGAAGTTGGCATTAAGTCTGTTGTCGTCCCGA<br>TCAAATTCATCGCGGAGTTCCTGGTTAACGGTGAGATTCTGAAG<br>CCGCGTATTGATAAAACTATGAAATACATTAACTCCGAAGATT<br>ACTACGGTAATCAGCATAACATCATCGTCGAGCACTTGCGTGA<br>TCAAAGCATTAAGATCGGTGACATCTTTAACGAAGATAAGCTG<br>AGCGATGTAGGCCACCAGTATGCGAACAATGACAAATTTCGCC<br>TGAATCCGGAAGTCAGCTACTTTACGAATAAGCGCACCCGTGG<br>TCCACTGGGTATCCTGAGCAATTATGTTAAAACCCTGTTGATTT<br>CCATGTACTGCTCCAAAACGTTCCTGGACGACAGCAACAAGCG<br>CAAAGTTCTGGCGATCGACTTCGGTAATGGTGCCGATCTGGAG<br>AAGTACTTTTATGGTGAGATCGCATTGCTGGTTGCTACCGACCC<br>GGATGCAGATGCGATCGCCCGTGGCAACGAGCGTTACAATAAG<br>CTGAATAGCGGTATCAAGACCAAATACTACAAATTCGACTATA<br>TTCAAGAGACGATCCGCTCGGACACCTTTGTATCCAGCGTGCGT<br>GAGGTGTTTTACTTCGGTAAATTCAACATCATTGACTGGCAATT<br>CGCCATTCACTATAGCTTTCACCCACGCCACTATGCGACGGTCA |

TABLE 3 -continued

SUMO-GT Fusion

| | |
|---|---|
| | TGAACAACCTGTCTGAGCTGACCGCGAGCGGCGGTAAAGTTCT<br>GATCACCACGATGGACGGTGACAAGCTGTCTAAACTGACCGAC<br>AAAAAGACCTTCATTATTCACAAAAATCTCCCGTCGAGCGAGA<br>ATTACATGTCCGTCGAAAAGATTGCGGACGACCGTATTGTTGTC<br>TACAACCCGAGCACTATGTCGACCCCAATGACCGAGTATATCA<br>TCAAAAAGAATGACATTGTGCGTGTCTTTAATGAATACGGTTTT<br>GTGCTGGTCGACAACGTCGATTTTGCGACCATCATCGAGAGAA<br>GCAAGAAATTCATTAATGGCGCTTCTACGATGGAAGATCGCCC<br>GAGCACGCGTAACTTCTTTGAGCTGAATCGTGGCGCGATTAAG<br>TGCGAGGGCCTGGACGTCGAGGATCTGCTGTCGTATTACGTGG<br>TTTATGTGTTTAGCAAACGTTAATGA (SEQ ID NO: 4) |
| SUMO-GT large<br>subunit protein<br>with His tag and<br>linker | MGHHHHHHGSLQEEKPKEGVKTENDHINLKVAGQDGSVVQFKIK<br>RHTPLSKLMKAYCERQGLSMRQIRFRFDGQPINETDTPAQLEMED<br>EDTIDVFQQQTGGMDANVVSSSTIATYIDALAKNASELEQRSTAY<br>EINNELELVFIKPPLITLTNVVNISTIQESFIRFTVTNKEGVKIRTKIPL<br>SKVHGLDVKNVQLVDAIDNIVWEKKSLVTENRLHKECLLRLSTEE<br>RHIFLDYKKYGSSIRLELVNLIQAKTKNFTIDFKLKYFLGSGAQSKS<br>SLLHAINHPKSRPNTSLEIEFTPRDNETVPYDELIKELTTLSRHIFMA<br>SPENVILSPPINAPIKTFMLPKQDIVGLDLENLYAVTKTDGIPITIRV<br>TSNGLYCYFTHLGYIIRYPVKRIIDSEVVVFGEAVKDKNWTVYLIK<br>LIEPVNAINDRLEESKYVESKLVDICDRIVFKSKKYEGPFTTTSEVV<br>DMLSTYLPKQPEGVILFYSKGPKSNIDFKIKKENTIDQTANVVFRY<br>MSSEPIIFGESSIFVEYKKFSNDKGFPKEYGSGKIVLYNGVNYLNNI<br>YCLEYINTHNEVGIKSVVVPIKFIAEFLVNGEILKPRIDKTMKYINSE<br>DYYGNQHNIIVEHLRDQSIKIGDIFNEDKLSDVGHQYANNDKFRL<br>NPEVSYFTNKRTRGPLGILSNYVKTLLISMYCSKTFLDDSNKRKVL<br>AIDFGNGADLEKYFYGEIALLVATDPDADAIARGNERYNKLNSGI<br>KTKYYKFDYIQETIRSDTFVSSVREVFYFGKFNIIDWQFAIHYSFHP<br>RHYATVMNNLSELTASGGKVLITTMDGDKLSKLTDKKTFIIHKNL<br>PSSENYMSVEKIADDRIVVYNPSTMSTPMTEYIIKKNDIVRVFNEY<br>GFVLVDNVDFATIIERSKKFINGASTMEDRPSTRNFFELNRGAIKCE<br>GLDVEDLLSYYVVYVFSKR (SEQ ID NO: 8) |

In some embodiments, the SUMO-GT fusion protein comprises SEQ ID NO: 8. In some embodiments, the SUMO-GT fusion protein is a heterodimer comprising SEQ ID NO: 8 and SEQ ID NO: 7. In some embodiments, the GT enzyme of the invention may be a homologue or analogue of one or the other of the GT large and small subunits. For example, a homologue or analogue of the SUMO-GT fusion protein may be a modified SUMO-GT fusion protein containing one or more amino acid substitutions, deletions, and/or insertions as compared to SEQ ID NO: 8 and/or SEQ ID NO: 7, while retaining substantial GT protein activity. Thus, in some embodiments, a SUMO-GT fusion protein suitable for the present invention is substantially homologous to the heterodimer comprising the GT small subunit (SEQ ID NO: 7) and the fusion of SUMO and the GT large subunit (SEQ ID NO: 8). In some embodiments, an enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 8 and SEQ ID NO: 7. In some embodiments, an enzyme suitable for the present invention is substantially identical to the heterodimer comprising the GT small subunit (SEQ ID NO: 7) and the fusion of SUMO and the GT large subunit (SEQ ID NO: 8). In some embodiments, an enzyme suitable for the present invention contains a fragment or a portion of a GT protein covalently bound to a SUMO protein.

Production of SUMO-GT Fusion Protein

Host Cells

As used herein, the term "host cells" refers to cells that can be used to produce a SUMO-GT fusion protein. In particular, host cells are suitable for producing a SUMO-GT fusion protein at a large scale. In some embodiments, host cells are able to produce SUMO-GT fusion protein in an amount of or greater than about 5 picogram/cell/day (e.g., greater than about 10, 15, 20, 25, 30, 35, 40, 45, 50, 55, 60, 65, 70, 75, 80, 85, 90, 95, or 100 picogram/cell/day). In some embodiments, host cells are able to produce SUMO-GT fusion protein in an amount ranging from about 5-100 picogram/cell/day (e.g., about 5-90 picogram/cell/day, about 5-80 picogram/cell/day, about 5-70 picogram/cell/day, about 5-60 picogram/cell/day, about 5-50 picogram/cell/day, about 5-40 picogram/cell/day, about 5-30 picogram/cell/day, about 10-90 picogram/cell/day, about 10-80 picogram/cell/day, about 10-70 picogram/cell/day, about 10-60 picogram/cell/day, about 10-50 picogram/cell/day, about 10-40 picogram/cell/day, about 10-30 picogram/cell/day, about 20-90 picogram/cell/day, about 20-80 picogram/cell/day, about 20-70 picogram/cell/day, about 20-60 picogram/cell/day, about 20-50 picogram/cell/day, about 20-40 picogram/cell/day, about 20-30 picogram/cell/day).

Suitable host cells can be derived from a variety of organisms, including, but not limited to, bacteria, yeast, insects, plants, birds (e.g., avian systems), amphibians, and mammals. In some embodiments, host cells are non-mammalian cells. Non-limiting examples of non-mammalian host cells suitable for the present invention include cells and cell lines derived from *Escherichia coli, Salmonella typhimurium, Bacillus subtilis, Bacillus lichenifonnis, Bacteroides fragilis, Clostridia perfringens, Clostridia difficile* for bacteria; *Pichia pastoris, Pichia methanolica, Pichia angusta, Schizosacccharomyces pombe, Saccharomyces cerevisiae,* and *Yarrowia lipolytica* for yeast; *Sodoptera frugiperda, Trichoplusis ni, Drosophila melangoster* and *Manduca sexta* for insects; and *Xenopus Laevis* from amphibian.

In some embodiments, host cells are mammalian cells. Any mammalian cell susceptible to cell culture, and to expression of polypeptides, may be utilized in accordance with the present invention as a host cell. Non-limiting examples of mammalian cells that may be used in accordance with the present invention include human embryonic kidney 293 cells (HEK293), HeLa cells; BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human fibrosarcomacell line (e.g., HT-1080); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells +/−DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; a human hepatoma line (Hep G2), human cell line CAP and AGE1.HN, and Glycotope's panel.

Additionally, any number of available hybridoma cell lines may be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

Expression Vectors

Various nucleic acid constructs can be used to express SUMO-GT fusion protein described herein in host cells. A suitable vector construct typically includes, in addition to SUMO-GT fusion protein-encoding sequences (also referred to as SUMO-GT fusion transgene), regulatory sequences, gene control sequences, promoters, non-coding sequences and/or other appropriate sequences for expression of the protein and, optionally, for replication of the construct. Typically, the coding region is operably linked with one or more of these nucleic acid components.

"Regulatory sequences" typically refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, 5' untranslated sequences, translation leader sequences, introns, and 3' untranslated sequences such as polyadenylation recognition sequences. Sometimes, "regulatory sequences" are also referred to as "gene control sequences."

"Promoter" typically refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions.

The "3' non-coding sequences" typically refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The "translation leader sequence" or "5' non-coding sequences" typically refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

Typically, the term "operatively linked" refers to the association of two or more nucleic acid fragments on a single nucleic acid fragment so that the function of one is affected by the other. For example, a promoter is operatively linked with a coding sequence when it is capable of affecting the expression of that coding sequence (i.e., that the coding sequence is under the transcriptional control of the promoter). Coding sequences can be operatively linked to regulatory sequences in sense or antisense orientation.

The coding region of a transgene may include one or more silent mutations to optimize codon usage for a particular cell type. For example, the codons of an SUMO-GT fusion transgene may be optimized for expression in a bacterial cell. In some embodiments, the codons of an SUMO-GT fusion transgene may be optimized for expression in an *E. coli* cell. In some embodiments, the codons of an SUMO-GT fusion transgene may be optimized for expression in a mammalian cell. In some embodiments, the codons of an SUMO-GT fusion transgene may be optimized for expression in a human cell.

Optionally, a construct may contain additional components such as one or more of the following: a splice site, an enhancer sequence, a selectable marker gene under the control of an appropriate promoter, an amplifiable marker gene under the control of an appropriate promoter, and a matrix attachment region (MAR) or other element known in the art that enhances expression of the region where it is inserted.

Once transfected or transduced into host cells, a suitable vector can express extrachromosomally (episomally) or integrate into the host cell's genome.

In some embodiments, a DNA construct that integrates into the cell's genome, it need include only the transgene nucleic acid sequences. In that case, the express of the transgene is typically controlled by the regulatory sequences at the integration site. Optionally, it can include additional various regulatory sequences described herein.

Culture Medium and Conditions

The term "medium" and "culture medium" as used herein refers to a general class of solution containing nutrients suitable for maintaining and/or growing cells in vitro. Typically, medium solutions provide, without limitation, essential and nonessential amino acids, vitamins, energy sources, lipids, and trace elements required by the cell for at least minimal growth and/or survival. In other embodiments, the medium may contain an amino acid(s) derived from any source or method known in the art, including, but not limited to, an amino acid(s) derived either from single amino acid addition(s) or from a peptone or protein hydrolysate addition(s) (including animal or plant source(s)). Vitamins such as, but not limited to, Biotin, Pantothenate, Choline Chloride, Folic Acid, Myo-Inositol, Niacinamide, Pyridoxine, Riboflavin, Vitamin B12, Thiamine, Putrescine and/or combinations thereof. Salts such as, but not limited to, $CaCl_2$, KCl, $MgCl_2$, NaCl, Sodium Phosphate Monobasic, Sodium Phosphate Dibasic, Sodium Selenite, $CuSO_4$, $ZnCl_2$ and/or combinations thereof. Fatty acids such as, but not limited to, Arachidonic Acid, Linoleic Acid, Oleic Acid, Lauric Acid, Myristic Acid, as well as Methyl-beta-Cyclodextrin and/or combinations thereof). In some embodiments, medium comprises additional components such as glucose, glutamine, Na-pyruvate, insulin or ethanolamine, a protective agent such as Pluronic F68. In some embodiments, the medium may also contain components that enhance growth and/or survival above the minimal rate, including hormones and growth factors. Medium may also comprise one or more buffering agents. The buffering agents may be designed and/or selected to maintain the culture at a particular pH (e.g., a physiological pH, (e.g., pH 6.8 to pH 7.4)). A variety of buffers suitable for culturing cells are known in the art and may be used in the methods. Suitable buffers (e.g., bicarbonate buffers, HEPES buffer, Good's buffers, etc.) are those that have the capacity and efficiency for maintaining physiological pH despite changes in carbon dioxide concentration associated with cellular respiration. The solution is preferably formulated to a pH and salt concentration optimal for cell survival and proliferation.

In some embodiments, medium may be a chemically defined medium. As used herein, the term "chemically-defined nutrient medium" refers to a medium of which substantially all of the chemical components are known. In some embodiments, a chemically defined nutrient medium is free of animal-derived components. In some cases, a chemically-defined medium comprises one or more proteins (e.g., protein growth factors or cytokines.) In some cases, a chemically-defined nutrient medium comprises one or more protein hydrolysates. In other cases, a chemically-defined nutrient medium is a protein-free media, i.e., a serum-free media that contains no proteins, hydrolysates or components of unknown composition.

Typically, a chemically defined medium can be prepared by combining various individual components such as, for example, essential and nonessential amino acids, vitamins, energy sources, lipids, salts, buffering agents, and trace elements, at predetermined weight or molar percentages or ratios. Exemplary serum-free, in particular, chemically-defined media are described in US Pub. No. 2006/0148074, the disclosure of which is hereby incorporated by reference.

In some embodiments, a chemically defined medium suitable for the present invention is a commercially available medium such as, but not limited to, Terrific Broth, Cinnabar, 2xYT or LB. In some embodiments, a chemically defined medium suitable for the present invention is a mixture of one or more commercially available chemically defined mediums. In various embodiments, a suitable medium is a mixture of two, three, four, five, six, seven, eight, nine, ten, or more commercially available chemically defined media. In some embodiments, each individual commercially available chemically defined medium (e.g., such as those described herein) constitutes, by weight, 1%, 2.5%, 5%, 7.5%, 10%, 12.5%, 15%, 20%, 25%, 30%, 35%, 40%, 45%, 50%, 55%, 60%, 65%, 70%, 75%, 80%, 85%, 90%, 95%, or more, of the mixture. Ratios between each individual component medium may be determined by relative weight percentage present in the mixture. In some embodiments, protein expression is increased with the addition of IPTG to repress the promoter.

In some embodiments, a chemically defined medium may be supplemented by one or more animal derived components. Such animal derived components include, but are not limited to, fetal calf serum, horse serum, goat serum, donkey serum, human serum, and serum derived proteins such as albumins (e.g., bovine serum albumin or human serum albumin).

The present invention provides a method of producing SUMO-GT fusion protein at a large scale. Typical large-scale procedures for producing a fusion polypeptide of interest include batch cultures and fed-batch cultures. Batch culture processes traditionally comprise inoculating a large-scale production culture with a seed culture of a particular cell density, growing the cells under conditions (e.g., suitable culture medium, pH, and temperature) conducive to cell growth, viability, and/or productivity, harvesting the culture when the cells reach a specified cell density, and purifying the expressed polypeptide. Fed-batch culture procedures include an additional step or steps of supplementing the batch culture with nutrients and other components that are consumed during the growth of the cells. In some embodiments, a large-scale production method according to the present invention uses a fed-batch culture system.

Purification of Expressed SUMO-GT Fusion Protein

Various methods may be used to purify or isolate SUMO-GT fusion protein produced according to various methods described herein. In some embodiments, the expressed SUMO-GT fusion protein is secreted into the medium and thus cells and other solids may be removed, as by centrifugation or filtering for example, as a first step in the purification process. Alternatively or additionally, the expressed SUMO-GT fusion protein is bound to the surface of the host cell. In this embodiment, the host cells (for example, bacterials cells) expressing the polypeptide or protein are lysed for purification. Lysis of host cells (e.g., bacterials cells) can be achieved by any number of means well known to those of ordinary skill in the art, including physical disruption by glass beads and exposure to high pH conditions.

The SUMO-GT fusion protein may be isolated and purified by standard methods including, but not limited to, chromatography (e.g., ion exchange, affinity, size exclusion, and hydroxyapatite chromatography), gel filtration, centrifugation, or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference). For immunoaffinity chromatography in particular, the protein may be isolated by binding it to an affinity column comprising antibodies that were raised against that protein and were affixed to a stationary support. Protease inhibitors such as phenyl methyl sulfonyl fluoride (PMSF), leupeptin, pepstatin or aprotinin may be added at any or all stages in order to reduce or eliminate degradation of the polypeptide or protein during the purification process. Protease inhibitors are particularly desired when cells must be lysed in order to isolate and purify the expressed polypeptide or protein.

Solubility

Various methods may be used to determine the solubility of a protein in an expression system. In an exemplary method, bacteria are spun down and resuspended in a mild lysis buffer containing 1% IGEPAL and protease inhibitors. Lysis is supported by repeated freezing and thawing the bacteria. Soluble and insoluble fraction are separated by centrifigation. To determine the total amount of recombinant protein the same volume of bacterial culture is spun down and lysed in the same amount of lysis buffer containing 1% IGEPAL and 0.1% SDS. Soluble and total protein are analyzed by SDS-PAGE, with western blotting if necessary. In some embodiments, the expression system is *E. coli*. In some embodiments, solubility of GT is improved when it has been produced as a fusion protein. In some embodiments, the fusion protein is a SUMO-GT fusion protein. In some embodiments, the SUMO-GT fusion protein has increased solubility compared to the non-fusion GT protein. In some embodiments, the increased solubility of the SUMO-GT fusion protein compared to the non-fusion GT protein is observed during shake flask production of the SUMO-GT fusion protein. In some embodiments, the increased solubility of the SUMO-GT fusion protein compared to the non-fusion GT protein is observed during fermentation production of the SUMO-GT fusion protein.

Use of SUMO-GT Fusion in mRNA Capping

Production of Capped mRNAs

According to the present invention, a SUMO-GT fusion protein described herein may be used to produce capped mRNAs by in vitro transcription. Various in vitro transcription assays are available in the art and can be used to practice the present invention. For example, in vitro transcription was originally developed by Krieg and Melton (METHODS ENZYMOL., 1987, 155: 397-415) for the synthesis of RNA using an RNA phage polymerase. Typically these reactions include at least a phage RNA polymerase (T7, T3 or SP6), a DNA template containing a phage polymerase promoter, nucleotides (ATP, CTP, GTP and UTP), and a buffer containing a magnesium salt. RNA synthesis yields may be optimized by increasing nucleotide concentrations, adjusting magnesium concentrations and by including inorganic pyrophosphatase (U.S. Pat. No. 5,256,555; Gurevich, et al., ANAL. BIOCHEM. 195: 207-213 (1991); Sampson, J. R. and Uhlenbeck, O. C., PROC. NATL. ACAD. SCI. USA. 85, 1033-1037 (1988); Wyatt, J. R., et al., BIOTECHNIQUES, 11: 764-769 (1991)). The RNA synthesized in these reactions is usually characterized by a 5' terminal nucleotide that has a triphosphate at the 5' position of the ribose. Typically, depending on the RNA polymerase and promoter combination used, this nucleotide is a guanosine, although it can be an adenosine (see e.g., Coleman, T. M., et al., NUCLEIC ACIDS RES., 32: e14 (2004)). In these reactions, all four nucleotides are typically included at equimolar concentrations and none of them is limiting.

Some embodiment of the invention are batch reactions—that is, all components are combined and then incubated at about 37° C. to promote the polymerization of the RNA until the reaction terminates. Typically, a batch reaction is used for convenience and to obtain as much RNA as needed from such reactions for their experiments. In some embodiments, a "fed-batch" system (see, e.g., JEFFREY A. KERN, BATCH AND FED-BATCH STRATEGIES FOR LARGE-SCALE PRODUCTION OF RNA BY IN VITRO TRANSACTION (University of Colorado) (1997)) is used to increase the efficiency of the in vitro transcription reaction. All components are combined, but then additional amounts of some of the reagents are added over time, such as the nucleotides and magnesium, to try to maintain constant reaction conditions. In addition, in some embodiments, the pH of the reaction may be held at 7.4 by monitoring it over time and adding KOH as needed.

To synthesize a capped RNA by in vitro transcription, a cap analog (e.g., N-7 methyl GpppG; i.e., m$^7$GpppG) is included in the transcription reaction. In some embodiments, the cap analog will be incorporated at the 5' terminus by the enzyme guanylyl transferase. In some embodiments, the guanylyl transferase is a fusion protein. In some embodiments, the guanylyl transferase fusion protein formed when a guanylyl transferase is covalently linked to a SUMO protein. In some embodiments, the cap analog will be incorporated only at the 5' terminus because it does not have a 5' triphosphate. In some embodiments using a T7, T3 and SP6 RNA polymerase, the +1 nucleotide of their respective promoters is usually a G residue and if both GTP and m$^7$GpppG are present in equal concentrations in the transcription reaction, then they each have an equal chance of being incorporated at the +1 position. In some embodiments, m$^7$GpppG is present in these reactions at several-fold higher concentrations than the GTP to increase the chances that a transcript will have a 5' cap. In some embodiments, a mMESSAGE mMACHINE® kit (Cat. #1344, Ambion, Inc.) is used according to manufacturer's instructions, where it is recommended that the cap to GTP ratio be 4:1 (6 mM: 1.5 mM). In some embodiments, as the ratio of the cap analog to GTP increases in the reaction, the ratio of capped to uncapped RNA increases proportionally. Considerations of capping efficiency must be balanced with considerations of yield. Increasing the ratio of cap analog to GTP in the transcription reaction produces lower yields of total RNA because the concentration of GTP becomes limiting when holding the total concentration of cap and GTP constant. Thus, the final RNA yield is dependent on GTP concentration, which is necessary for the elongation of the transcript. The other nucleotides (ATP, CTP, UTP) are present in excess.

Figure 1B:
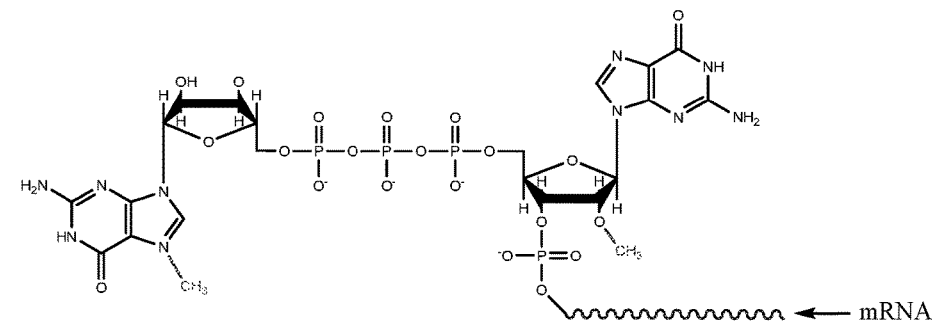

In particular embodiments, mRNA are synthesized by in vitro transcription from a plasmid DNA template encoding a gene of choice. In some embodiments, in vitro transcription includes addition of a 5' cap structure, Cap1 (FIG. 1B), which has a 2'-O-methyl residue at the 2' OH group of the ribose ring of base 1, by enzymatic conjugation of GTP via a guanylyl transferase. In some embodiments, in vitro transcription includes addition of a 5' cap structure, Cap0 (FIG. 1A), which lacks the 2'-O-methyl residue, by enzymatic conjugation of GTP via a guanylyl transferase. In some embodiments, in vitro transcription includes addition of a 5' cap of any of the cap structures disclosed herein by enzymatic conjugation of GTP via a guanylyl transferase.

Capping Efficiency

The present invention significantly increases capping efficiency. In some embodiments, the use of a SUMO-GT fusion protein in an in vitro capping assay results in at least about 70%, 75%, 80%, 85%, 90%, 95%, 96%, 97%, 98%, or 99% capped mRNA. In some embodiments, the use of a SUMO-GT fusion protein in an in vitro capping assay results in substantially 100% capped mRNA. In some embodiments, the use of a SUMO-GT fusion protein in an in vitro capping assay results in increase of mRNA capping efficiency by at least about 20%, 30%, 40%, 50%, 60%, 70%, 80%, 90%, 95%, 1-fold, 1.5-fold, 2-fold, 2.5-fold, 3-fold, 3.5-fold, 4-fold, 4.5-fold, or 5-fold as compared to a control assay using a non-fusion GT protein but under otherwise identical conditions.

In addition, the present invention permits large-scale production of capped mRNA with high efficiency. In some embodiments, capped mRNA is produced at a scale of or greater than 1 gram, 5 grams, 10 grams, 15 grams, 20 grams, 25 grams, 30 grams, 35 grams, 40 grams, 45 grams, 50 grams, 75 grams, 100 grams, 150 grams, 200 grams, 250 grams, 300 grams, 350 grams, 400 grams, 450 grams, 500 grams, 550 grams, 600 grams, 650 grams, 700 grams, 750 grams, 800 grams, 850 grams, 900 grams, 950 grams, 1 kg, 2.5 kg, 5 kg, 7.5 kg, 10 kg, 25 kg, 50 kg, 75 kg, or 100 kg per batch.

Methods of estimating capping efficiency are known in the art. For example, the T7 RNA polymerase can be incubated with a cap dinucleotide, all four ribonucleotide triphosphates, [$\alpha$-$^{32}$P]GTP, and a short DNA template in which G is the first ribonucleotide specified after the promoter (see Grudzien, E. et al. "*Novel cap analogs for in vitro synthesis of mRNA with high translation efficiency*", RNA, 10: 1479-1487 (2004)). Any nucleotide on the 5' side of a G residue acquires a $^{32}$P-labeled 3'-phosphate group after RNase T2 digestion by nearest-neighbor transfer. Anion exchange chromatography is then used to resolve labeled nucleoside 3'-monophosphates, resulting from internal positions in the RNA, from 5'-terminal products. 5'-terminal products are of two types. Uncapped RNAs yield labeled guanosine 5'-triphosphate 3'-monophosphate (p3Gp*; in which * indicates the labeled phosphate group). Capped RNAs yield various 5'-terminal structures, depending on the nature of the cap analog used (m$^7$Gp3Gp* and Gp3m$^7$Gp* when the cap analog is m$^7$Gp3G).

Improved methods of directly quantitating mRNA capping efficiency in a sample (e.g., a representative aliquot sample from an in vitro synthesis reaction) are provided in WO 2014/152673, which is incorporated herein by reference. Some embodiments comprise the use of a cap specific binding substance under conditions that permit the formation of a complex between the cap specific binding substance and the capped mRNA. The formation of a complex between the cap specific binding substance and the capped mRNA allows quantitative determination of the amount of the complex (i.e., capped mRNAs) relative to a positive control of capped products or negative control of uncapped products. In other words, binding indicates the amount of capped mRNA targets in the sample and the capping efficiency in a reaction from which the sample is derived. Thus, in some embodiments, the step of quantitatively determining the amount of the complex comprises performing an ELISA-type assay wherein the cap specific binding substance is an antibody or other protein that specifically binds an mRNA cap. Complex formation can be quantified by addition of a detection agent specific for the cap specific binding substance (e.g., a goat anti-mouse antibody that binds a mouse anti-m$^7$G antibody) and which produces a signal directly proportional to the amount of capped mRNA. Embodiments of the invention may be used to quantify the capping efficiency of a wide variety of RNA species, including in vitro transcribed mRNA, isolated eukaryotic mRNA, and viral RNA.

Additional improved methods of directly quantitating mRNA capping efficiency in a sample (e.g., a representative aliquot sample from an in vitro synthesis reaction) are provided in WO 2014/152659, which is incorporated herein by reference. Some embodiments of the invention comprise chromatographic methods of quantitating mRNA capping efficiency. These methods are based in part on the insights that the versatility of enzymatic manipulation can be used to increase the resolution of chromatographic separation of polynucleotides. Thus, by amplifying the power of chromatographic separation through enzymatic manipulation, embodiments of the invention increase the efficiency, quality and throughput of quantitation. For example, not only can the chromatographic methods described herein quantitate capping efficiency, they can also provide information on the modification of the cap (e.g., methylation status at particular cap positions). Thus, embodiments of the invention can simultaneously quantitate capping efficiency and the efficiency of cap modification (e.g., methylation efficiency). This quantification provides important characterization of an mRNA drug product that has significant impact on the protein production.

The invention will be more fully understood by reference to the following examples. They should not, however, be construed as limiting the scope of the invention. All literature citations are incorporated by reference.

EXAMPLES

Example 1: SUMO-GT Construct Design

```
Small ubiquitin-like modifier (SUMO) DNA:
                                               (SEQ ID NO: 1)
GAAGAGAAACCGAAAGAGGGCGTTAAGACCGAGAATGACCACATTAACCTGAAGG

TCGCTGGTCAAGATGGCAGCGTGGTGCAGTTTAAGATCAAGCGTCACACGCCGTTGA

GCAAGCTGATGAAGGCTTACTGCGAGCGTCAGGGTCTGAGCATGCGTCAGATCCGC

TTTCGTTTCGATGGCCAGCCGATCAATGAGACTGACACCCCAGCGCAACTGG

Guanylyl transferase (GT) large subunit DNA:
                                               (SEQ ID NO: 2)
AGATGGAAGATGAAGATACCATCGACGTCTTTCAGCAACAGACCGGTGGTATGGAT

GCTAACGTCGTTAGCAGCAGCACCATTGCGACTTACATTGATGCACTGGCCAAAAC

GCATCTGAGCTTGAGCAGCGCAGCACCGCCTACGAGATCAATAACGAATTGGAGCT

GGTTTTCATTAAACCGCCGCTGATCACGCTGACGAACGTCGTGAACATTAGCACGAT

TCAAGAGAGCTTTATTCGTTTCACCGTTACCAATAAAGAAGGCGTGAAGATCCGTAC

CAAGATTCCGCTGAGCAAAGTGCATGGTCTGGACGTGAAAAATGTGCAGCTGGTTG

ATGCGATCGATAACATCGTGTGGGAGAAGAAATCTTTGGTCACGGAAAATCGTCTG
```

-continued

```
CACAAGGAATGTCTGCTGCGTCTGTCAACCGAAGAACGCCACATCTTCCTGGACTAC

AAGAAGTATGGTTCCAGCATCCGTCTGGAACTGGTGAACCTGATTCAGGCAAAGAC

CAAGAACTTCACCATTGACTTCAAACTGAAGTATTTCCTGGGCTCTGGTGCACAGAG

CAAATCCAGCTTGTTGCACGCGATTAACCATCCGAAGAGCCGTCCGAATACGAGCCT

GGAGATCGAATTCACGCCGCGTGATAACGAAACCGTTCCGTACGATGAGCTGATTA

AGAACTGACGACGTTGAGCCGCCACATCTTTATGGCCAGCCCGGAAAACGTGATC

CTTAGCCCGCCTATCAATGCGCCGATTAAAACCTTTATGTTACCGAAACAAGACATT

GTGGGTCTGGACCTGGAAAACCTGTACGCGGTCACCAAAACGGACGGCATTCCGAT

CACGATTCGTGTTACCAGCAATGGTCTGTACTGCTATTTCACTCATTTGGGCTATATC

ATTCGTTATCCGGTGAAACGCATCATTGATTCTGAGGTTGTCGTTTTCGGCGAAGCA

GTCAAGGACAAGAATTGGACTGTGTACCTGATCAAATTGATTGAACCGGTTAACGCC

ATCAATGACCGCCTGGAAGAGTCGAAATATGTTGAAAGCAAACTGGTGGATATTTG

TGATCGTATCGTGTTCAAGAGCAAGAAATATGAAGGCCCGTTCACCACGACCAGCG

AAGTTGTTGACATGCTGAGCACCTATCTGCCGAAACAACCTGAGGGTGTGATTCTGT

TTTACTCCAAGGGTCCGAAGAGCAACATTGATTTCAAAATCAAGAAAGAGAATACC

ATTGATCAGACCGCCAACGTTGTGTTCCGCTATATGTCCAGCGAGCCTATCATTTTCG

GTGAGTCGAGCATCTTTGTTGAATACAAAAAGTTTAGCAACGATAAGGGTTTTCCGA

AAGAATACGGTTCCGGTAAGATTGTGTTGTACAACGGCGTCAATTATCTGAACAACA

TCTACTGTCTGGAGTACATCAATACCCATAACGAAGTTGGCATTAAGTCTGTTGTCG

TCCCGATCAAATTCATCGCGGAGTTCCTGGTTAACGGTGAGATTCTGAAGCCGCGTA

TTGATAAAACTATGAAATACATTAACTCCGAAGATTACTACGGTAATCAGCATAACA

TCATCGTCGAGCACTTGCGTGATCAAAGCATTAAGATCGGTGACATCTTTAACGAAG

ATAAGCTGAGCGATGTAGGCCACCAGTATGCGAACAATGACAAATTTCGCCTGAAT

CCGGAAGTCAGCTACTTTACGAATAAGCGCACCCGTGGTCCACTGGGTATCCTGAGC

AATTATGTTAAAACCCTGTTGATTTCCATGTACTGCTCCAAAACGTTCCTGGACGAC

AGCAACAAGCGCAAAGTTCTGGCGATCGACTTCGGTAATGGTGCCGATCTGGAGAA

GTACTTTTATGGTGAGATCGCATTGCTGGTTGCTACCGACCCGGATGCAGATGCGAT

CGCCCGTGGCAACGAGCGTTACAATAAGCTGAATAGCGGTATCAAGACCAAATACT

ACAAATTCGACTATATTCAAGAGACGATCCGCTCGGACACCTTTGTATCCAGCGTGC

GTGAGGTGTTTTACTTCGGTAAATTCAACATCATTGACTGGCAATTCGCCATTCACTA

TAGCTTTCACCCACGCCACTATGCGACGGTCATGAACAACCTGTCTGAGCTGACCGC

GAGCGGCGGTAAAGTTCTGATCACCACGATGGACGGTGACAAGCTGTCTAAACTGA

CCGACAAAAAGACCTTCATTATTCACAAAAATCTCCCGTCGAGCGAGAATTACATGT

CCGTCGAAAAGATTGCGGACGACCGTATTGTTGTCTACAACCCGAGCACTATGTCGA

CCCCAATGACCGAGTATATCATCAAAAAGAATGACATTGTGCGTGTCTTTAATGAAT

ACGGTTTTGTGCTGGTCGACAACGTCGATTTTGCGACCATCATCGAGAGAAGCAAGA

AATTCATTAATGGCGCTTCTACGATGGAAGATCGCCCGAGCACGCGTAACTTCTTTG

AGCTGAATCGTGGCGCGATTAAGTGCGAGGGCCTGGACGTCGAGGATCTGCTGTCG

TATTACGTGGTTTATGTGTTTAGCAAACGTTAATGA
```

-continued

Guanylyl transferase (GT) small subunit DNA:

(SEQ ID NO: 3)
ATGGACGAAATTGTCAAGAATATCCGTGAAGGTACCCACGTTTTACTGCCATTCTAC

GAGACGCTGCCGGAACTGAACCTGAGCCTGGGTAAAAGCCCTCTGCCGAGCCTGGA

GTATGGTGCGAACTATTTTCTGCAGATTTCCCGTGTAAACGATTTGAACCGCATGCC

GACGGACATGCTGAAACTGTTCACCCACGACATCATGCTGCCGGAATCTGATCTGGA

TAAAGTTTACGAGATCTTGAAAATCAATTCAGTGAAGTACTATGGCCGTAGCACCAA

GGCCGATGCGGTGGTCGCAGACCTGAGCGCGCGTAACAAACTGTTTAAACGTGAAC

GTGACGCAATTAAGAGCAATAACCATCTGACCGAGAACAATTTGTACATCAGCGAC

TACAAGATGTTGACTTTTGACGTGTTTCGTCCGCTGTTCGACTTTGTTAATGAGAAAT

ACTGCATTATCAAGCTGCCGACGTTGTTTGGTCGCGGCGTCATTGATACGATGCGCA

TTTACTGCTCTCTCTTCAAGAATGTGCGCCTGCTGAAGTGTGTCTCCGACAGCTGGCT

GAAAGATAGCGCTATTATGGTTGCGAGCGACGTGTGTAAAAAGAACCTGGATCTGT

TCATGAGCCACGTGAAGAGCGTTACCAAAAGCAGCAGCTGGAAAGACGTTAACAGC

GTCCAGTTCTCCATTCTGAATAACCCGGTCGATACCGAGTTTATCAACAAGTTCCTTG

AATTCAGCAATCGCGTTTATGAGGCCCTGTATTACGTTCATAGCCTGCTGTATAGCTC

CATGACCTCTGATAGCAAATCGATCGAGAATAAACACCAACGTCGTCTGGTGAAAC

TGCTGCTGTAATGA

SUMO-GT large subunit DNA construct with His tag and linker:

(SEQ ID NO: 4)
ATGGGCCATCATCATCACCATCACGGCAGCCTGCAAGAAGAGAAACCGAAAGAGGG

CGTTAAGACCGAGAATGACCACATTAACCTGAAGGTCGCTGGTCAAGATGGCAGCG

TGGTGCAGTTTAAGATCAAGCGTCACACGCCGTTGAGCAAGCTGATGAAGGCTTACT

GCGAGCGTCAGGGTCTGAGCATGCGTCAGATCCGCTTTCGTTTCGATGGCCAGCCGA

TCAATGAGACTGACACCCCAGCGCAACTGGAGATGGAAGATGAAGATACCATCGAC

GTCTTTCAGCAACAGACCGGTGGTATGGATGCTAACGTCGTTAGCAGCAGCACCATT

GCGACTTACATTGATGCACTGGCCAAAAACGCATCTGAGCTTGAGCAGCGCAGCAC

CGCCTACGAGATCAATAACGAATTGGAGCTGGTTTTCATTAAACCGCCGCTGATCAC

GCTGACGAACGTCGTGAACATTAGCACGATTCAAGAGAGCTTTATTCGTTTCACCGT

TACCAATAAAGAAGGCGTGAAGATCCGTACCAAGATTCCGCTGAGCAAAGTGCATG

GTCTGGACGTGAAAAATGTGCAGCTGGTTGATGCGATCGATAACATCGTGTGGGAG

AAGAAATCTTTGGTCACGGAAAATCGTCTGCACAAGGAATGTCTGCTGCGTCTGTCA

ACCGAAGAACGCCACATCTTCCTGGACTACAAGAAGTATGGTTCCAGCATCCGTCTG

GAACTGGTGAACCTGATTCAGGCAAAGACCAAGAACTTCACCATTGACTTCAAACT

GAAGTATTTCCTGGGCTCTGGTGCACAGAGCAAATCCAGCTTGTTGCACGCGATTAA

CCATCCGAAGAGCCGTCCGAATACGAGCCTGGAGATCGAATTCACGCCGCGTGATA

ACGAAACCGTTCCGTACGATGAGCTGATTAAAGAACTGACGACGTTGAGCCGCCAC

ATCTTTATGGCCAGCCCGGAAAACGTGATCCTTAGCCCGCCTATCAATGCGCCGATT

AAAACCTTTATGTTACCGAAACAAGACATTGTGGGTCTGGACCTGGAAAACCTGTAC

GCGGTCACCAAAACGGACGGCATTCCGATCACGATTCGTGTTACCAGCAATGGTCTG

TACTGCTATTTCACTCATTTGGGCTATATCATTCGTTATCCGGTGAAACGCATCATTG

ATTCTGAGGTTGTCGTTTTCGGCGAAGCAGTCAAGGACAAGAATTGGACTGTGTACC

TGATCAAATTGATTGAACCGGTTAACGCCATCAATGACCGCCTGGAAGAGTCGAAA

-continued

```
TATGTTGAAAGCAAACTGGTGGATATTTGTGATCGTATCGTGTTCAAGAGCAAGAAA

TATGAAGGCCCGTTCACCACGACCAGCGAAGTTGTTGACATGCTGAGCACCTATCTG

CCGAAACAACCTGAGGGTGTGATTCTGTTTTACTCCAAGGGTCCGAAGAGCAACATT

GATTTCAAAATCAAGAAAGAGAATACCATTGATCAGACCGCCAACGTTGTGTTCCGC

TATATGTCCAGCGAGCCTATCATTTTCGGTGAGTCGAGCATCTTTGTTGAATACAAA

AAGTTTAGCAACGATAAGGGTTTTCCGAAAGAATACGGTTCCGGTAAGATTGTGTTG

TACAACGGCGTCAATTATCTGAACAACATCTACTGTCTGGAGTACATCAATACCCAT

AACGAAGTTGGCATTAAGTCTGTTGTCGTCCCGATCAAATTCATCGCGGAGTTCCTG

GTTAACGGTGAGATTCTGAAGCCGCGTATTGATAAAACTATGAAATACATTAACTCC

GAAGATTACTACGGTAATCAGCATAACATCATCGTCGAGCACTTGCGTGATCAAAGC

ATTAAGATCGGTGACATCTTTAACGAAGATAAGCTGAGCGATGTAGGCCACCAGTA

TGCGAACAATGACAAATTTCGCCTGAATCCGGAAGTCAGCTACTTTACGAATAAGCG

CACCCGTGGTCCACTGGGTATCCTGAGCAATTATGTTAAAACCCTGTTGATTTCCAT

GTACTGCTCCAAAACGTTCCTGGACGACAGCAACAAGCGCAAAGTTCTGGCGATCG

ACTTCGGTAATGGTGCCGATCTGGAGAAGTACTTTTATGGTGAGATCGCATTGCTGG

TTGCTACCGACCCGGATGCAGATGCGATCGCCCGTGGCAACGAGCGTTACAATAAG

CTGAATAGCGGTATCAAGACCAAATACTACAAATTCGACTATATTCAAGAGACGAT

CCGCTCGGACACCTTTGTATCCAGCGTGCGTGAGGTGTTTTACTTCGGTAAATTCAA

CATCATTGACTGGCAATTCGCCATTCACTATAGCTTTCACCCACGCCACTATGCGAC

GGTCATGAACAACCTGTCTGAGCTGACCGCGAGCGGCGGTAAAGTTCTGATCACCA

CGATGGACGGTGACAAGCTGTCTAAACTGACCGACAAAAAGACCTTCATTATTCAC

AAAAATCTCCCGTCGAGCGAGAATTACATGTCCGTCGAAAAGATTGCGGACGACCG

TATTGTTGTCTACAACCCGAGCACTATGTCGACCCCAATGACCGAGTATATCATCAA

AAAGAATGACATTGTGCGTGTCTTTAATGAATACGGTTTTGTGCTGGTCGACAACGT

CGATTTTGCGACCATCATCGAGAGAAGCAAGAAATTCATTAATGGCGCTTCTACGAT

GGAAGATCGCCCGAGCACGCGTAACTTCTTTGAGCTGAATCGTGGCGCGATTAAGTG

CGAGGGCCTGGACGTCGAGGATCTGCTGTCGTATTACGTGGTTTATGTGTTTAGCAA

ACGTTAATGA
```

Small ubiquitin-like modifier (SUMO) protein:

(SEQ ID NO: 5)

EEKPKEGVKTENDHINLKVAGQDGSVVQFKIKRHTPLSKLMKAYCERQGLSMRQIRFRF

DGQPINETDTPAQLEMEDEDTIDVFQQQTGG

Guanylyl transferase (GT) large subunit protein:

(SEQ ID NO: 6)

MDANVVSSSTIATYIDALAKNASELEQRSTAYEINNELELVFIKPPLITLTNVVNISTIQES

FIRFTVTNKEGVKIRTKIPLSKVHGLDVKNVQLVDAIDNIVWEKKSLVTENRLHKECLLR

LSTEERHIFLDYKKYGSSIRLELVNLIQAKTKNFTIDFKLKYFLGSGAQSKSSLLHAINHP

KSRPNTSLEIEFTPRDNETVPYDELIKELTTLSRHIFMASPENVILSPPINAPIKTFMLPKQD

IVGLDLENLYAVTKTDGIPITIRVTSNGLYCYFTHLGYIIRYPVKRIIDSEVVVFGEAVKDK

NWTVYLIKLIEPVNAINDRLEESKYVESKLVDICDRIVFKSKKYEGPFTTTSEVVDMLST

YLPKQPEGVILFYSKGPKSNIDFKIKKENTIDQTANVVFRYMSSEPIIFGESSIFVEYKKFS

NDKGFPKEYGSGKIVLYNGVNYLNNIYCLEYINTHNEVGIKSVVVPIKFIAEFLVNGEILK

-continued
PRIDKTMKYINSEDYYGNQHNIIVEHLRDQSIKIGDIFNEDKLSDVGHQYANNDKFRLNP

EVSYFTNKRTRGPLGILSNYVKTLLISMYCSKTFLDDSNKRKVLAIDFGNGADLEKYFY

GEIALLVATDPDADAIARGNERYNKLNSGIKTKYYKFDYIQETIRSDTFVSSVREVFYFG

KFNIIDWQFAIHYSFHPRHYATVMNNLSELTASGGKVLITTMDGDKLSKLTDKKTFIIHK

NLPSSENYMSVEKIADDRIVVYNPSTMSTPMTEYIIKKNDIVRVFNEYGFVLVDNVDFAT

IIERSKKFINGASTMEDRPSTRNFFELNRGAIKCEGLDVEDLLSYYVVYVFSKR

Guanylyl transferase (GT) small subunit protein:
(SEQ ID NO: 7)
MDEIVKNIREGTHVLLPFYETLPELNLSLGKSPLPSLEYGANYFLQISRVNDLNRMPTDM

LKLFTHDIMLPESDLDKVYEILKINSVKYYGRSTKADAVVADLSARNKLFKRERDAIKS

NNHLTENNLYISDYKMLTFDVFRPLFDFVNEKYCIIKLPTLFGRGVIDTMRIYCSLFKNV

RLLKCVSDSWLKDSAIMVASDVCKKNLDLFMSHVKSVTKSSSWKDVNSVQFSILNNPV

DTEFINKFLEFSNRVYEALYYVHSLLYSSMTSDSKSIENKHQRRLVKLLL

SUMO-GT large subunit protein with His tag and linker:
(SEQ ID NO: 8)
MGHHHHHHGSLQEEKPKEGVKTENDHINLKVAGQDGSVVQFKIKRHTPLSKLMKAYC

ERQGLSMRQIRFRFDGQPINETDTPAQLEMEDEDTIDVFQQQTGGMDANVVSSSTIATYI

DALAKNASELEQRSTAYEINNELELVFIKPPLITLTNVVNISTIQESFIRFTVTNKEGVKIRT

KIPLSKVHGLDVKNVQLVDAIDNIVWEKKSLVTENRLHKECLLRLSTEERHIFLDYKKY

GSSIRLELVNLIQAKTKNFTIDFKLKYFLGSGAQSKSSLLHAINHPKSRPNTSLEIEFTPRD

NETVPYDELIKELTTLSRHIFMASPENVILSPPINAPIKTFMLPKQDIVGLDLENLYAVTKT

DGIPITIRVTSNGLYCYFTHLGYIIRYPVKRIIDSEVVVFGEAVKDKNWTVYLIKLIEPVNA

INDRLEESKYVESKLVDICDRIVFKSKKYEGPFTTTSEVVDMLSTYLPKQPEGVILFYS KG

PKSNIDFKIKKENTIDQTANVVFRYMSSEPIIFGESSIFVEYKKFSNDKGFPKEYGSGKIVL

YNGVNYLNNIYCLEYINTHNEVGIKSVVVPIKFIAEFLVNGEILKPRIDKTMKYINSEDYY

GNQHNIIVEHLRDQSIKIGDIFNEDKLSDVGHQYANNDKFRLNPEVSYFTNKRTRGPLGI

LSNYVKTLLISMYCSKTFLDDSNKRKVLAIDFGNGADLEKYFYGEIALLVATDPDADAI

ARGNERYNKLNSGIKTKYYKFDYIQETIRSDTFVSSVREVFYFGKFNIIDWQFAIHYSFHP

RHYATVMNNLSELTASGGKVLITTMDGDKLSKLTDKKTFIIHKNLPSSENYMSVEKIAD

DRIVVYNPSTMSTPMTEYIIKKNDIVRVFNEYGFVLVDNVDFATIIERSKKFINGASTMED

RPSTRNFFELNRGAIKCEGLDVEDLLSYYVVYVFSKR

Example 2: Production of SUMO-GT Protein

Shake Flask

Production of SUMO-GT fusion protein can be performed according to standard methods and procedures. For example, to test and compare expression of the GT and SUMO-GT fusion proteins, a single colony of the E. coli Rosetta strain (Novagen) containing each of the SUMO-eGFP plasmids was inoculated into 5 ml of Luria-Bertani (LB) media containing 100 μg/ml Kanamycin and 30 μg/m; chloramphenicol. This strain is derived from the lambda DE3 lysogen strain and carries a chromosomal copy of the IPTG-inducible T7 RNA polymerase along with tRNAs on a pACYC-based plasmid. The cells were grown at 37° C. overnight with shaking at 250 rpm. The next morning the overnight culture was transferred into 100 ml fresh medium to permit exponential growth. When the OD600 value reached ~0.6-0.7, protein expression was induced by addition of 1 mM IPTG (isopropropyl-β-D-thiogalactopyranoside), followed by prolonged cultivation at either 37° C. for 3 hours or 20° C. overnight (about 15 hours).

After the E. coli cells were harvested from LB medium (100 ml) by centrifugation (8,000×g for 10 min at 4° C.), the cell pellets were suspended in 6 ml of lysis buffer (PBS containing 300 mM NaCl, 10 mM imidazole, 0.1% Triton XlOO and 1 mM PMSF, pH 8.0). The cells were lysed by sonication (at 50% output for 5×30 second pulses). The sonication was conducted with the tube jacketed in wet ice and 1 min intervals between the pulse cycles to prevent heating. After the lysates were incubated with DNase and RNase (each at 40 μg/ml) for 15 min to digest nucleic acids, they were centrifuged at 20,000 g for 30 min at 4° C., and the supernatant (soluble protein fractions) was collected. The pellets was washed once with 6 ml of the lysis buffer to further extract the soluble fraction; the wash (6 ml) was combined with previous extract (6 ml) to make final volume of 12 ml for the soluble protein sample.

Insoluble protein samples were prepared from *E. coli* inclusion bodies. Briefly, after the extract containing soluble proteins were removed, the pellets containing inclusion bodies were suspended in the denaturing solubilization buffer (Novagen) that contained 50 mM CAPS (pH 11.0), 0.3% N-laurylsarcosine, and 1 mM DTT and incubated for 20 min at room temperature with shaking. The extract (insoluble protein fraction) was obtained by high-speed centrifugation (80,000×g for 20 min at 4° C.).

For detection of expressed proteins using SDS-PAGE, 5 µl of the samples prepared above were mixed with 3 µl of SDSPAGE sample buffer containing SDS and β-mercaptoethanol and were heated at 95° C. for 5 min to facilitate denaturation and reduction of proteins. Proteins were visualized using 15% SDS-polyacrylamide gels with Tris-Glycine running buffer and Coomassie blue staining.

Fermentation

The substantial increase in the solubility of the final SUMO-GT complexed enzyme was also reproduced by fermentation. Fermentation was performed according to standard methods and procedures. For example, fermentation methods for production of SUMO-GT fusion protein comprised cell lysis, Immobilized Metal Affinity Chromatography (IMAC), Cation Exchange Chromatography, Anion Exchange Chromatography, and Tangential Flow Filtration (TFF) formulation. Quality testing of the SUMO-GT fusion protein that resulted from fermentation comprised Reducing SDS PAGE to determine purity and identity, Reverse-Phase HPLC to determine purity, A280 measurement of concentration and *Limulus amebocyte* lysate (LAL) assay to test for endotoxin.

Figure 2:
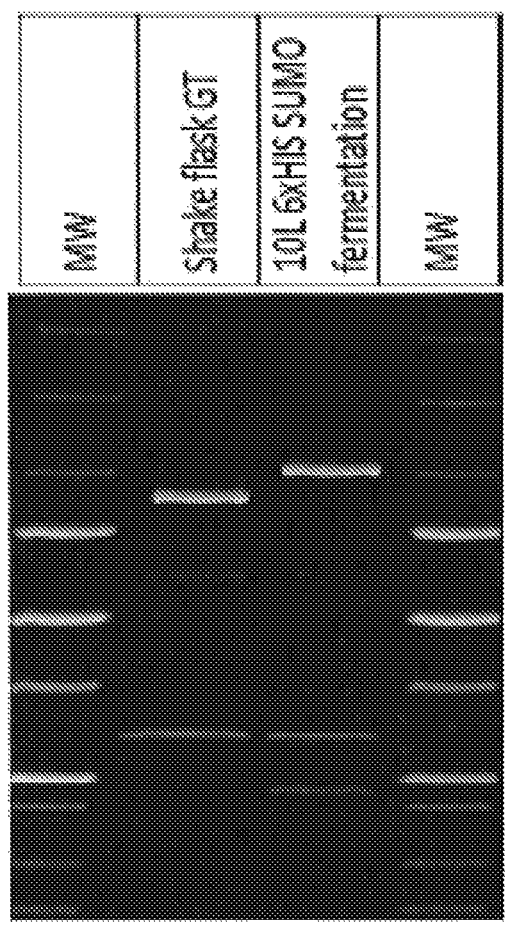
FIG. 2 demonstrates exemplary yield of soluble SUMO-GT protein produced by fermentation compared to that of GT protein produced via the shake flask method.

As shown in FIG. 2, the yield of soluble SUMO-GT protein produced by fermentation is comparable to that of GT protein produced via the shake flask method.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of producing a capped RNA or RNA analog oligonucleotide, comprising transferring and methylating a guanylyl molecule to the 5' end of the RNA or RNA analog oligonucleotide using a SUMO fusion guanylyl transferase comprising SEQ ID NO: 8 and SEQ ID NO: 7.

* * * * *